US012201134B2

(12) United States Patent
Sobel et al.

(10) Patent No.: US 12,201,134 B2
(45) Date of Patent: Jan. 21, 2025

(54) MICRO ENCAPSULATION USING HIGH-VOLTAGE, LOW-CURRENT, HIGH FREQUENCY ALTERNATING-CURRENT SPRAY ATOMIZATION

(71) Applicant: FONA TECHNOLOGIES, LLC, Geneva, IL (US)

(72) Inventors: Robert M. Sobel, Elburn, IL (US); Chin-Ping Su, Naperville, IL (US)

(73) Assignee: FONA TECHNOLOGIES, LLC

(*) Notice: Subject to any disclaimer, the term of this patent is extended or adjusted under 35 U.S.C. 154(b) by 644 days.

(21) Appl. No.: 17/245,249

(22) Filed: Apr. 30, 2021

(65) Prior Publication Data

US 2021/0244059 A1 Aug. 12, 2021

Related U.S. Application Data

(63) Continuation-in-part of application No. PCT/US2019/059506, filed on Nov. 1, 2019.
(Continued)

(51) Int. Cl.
    *B01D 1/18* (2006.01)
    *A23L 27/00* (2016.01)
    (Continued)

(52) U.S. Cl.
    CPC ............... *A23L 27/72* (2016.08); *B01D 1/18* (2013.01); *B01J 2/04* (2013.01); *B01J 13/043* (2013.01)

(58) Field of Classification Search
    CPC ..... B01D 1/18; A23L 27/72; B01J 2/04; B01J 13/043
    See application file for complete search history.

(56) References Cited

U.S. PATENT DOCUMENTS 3,949,096 A * 4/1976 Johnson .................... A61K 9/50
                                                    426/294
4,290,091 A * 9/1981 Malcolm ............... B05B 5/0532
                                                    361/228
(Continued)

OTHER PUBLICATIONS

International Search Report and Written Opinion, Application No. PCT/US2019/059506, mailed Jan. 15, 2020, 12 pages.
(Continued)

*Primary Examiner* — Jonathan Miller
(74) *Attorney, Agent, or Firm* — MCANDREWS HELD & MALLOY, LTD

(57) ABSTRACT

Disclosed is a spray drying system and process for encapsulating a core material, such as a volatile flavor oil, within a carrier or wall material. The process is achieved by atomizing a liquid emulsion comprising the core material, the wall material, and a liquid solvent, applying a high-voltage, low-current, high frequency alternating-current charge or a high-voltage, low-current, low frequency alternating-current charge at the site of atomization, and drying the atomized emulsion into an encapsulated, free-flowing powder. Applying a high-voltage, low current alternating-current at the site of atomization allows the spray drying to be accomplished at significantly reduced temperatures, in particular, at inlet temperatures in the range of 25° C. to 150° C., and outlet temperatures in the range of 25° C. to 110° C. The low drying temperatures impart improvements in the resulting encapsulated powdered product, including better retention of volatile flavor components, a flavor profile comparable to that of the starting liquid formulation, and better hydration and dissolution in water-based applications.

12 Claims, 15 Drawing Sheets

Related U.S. Application Data

Figure 1:
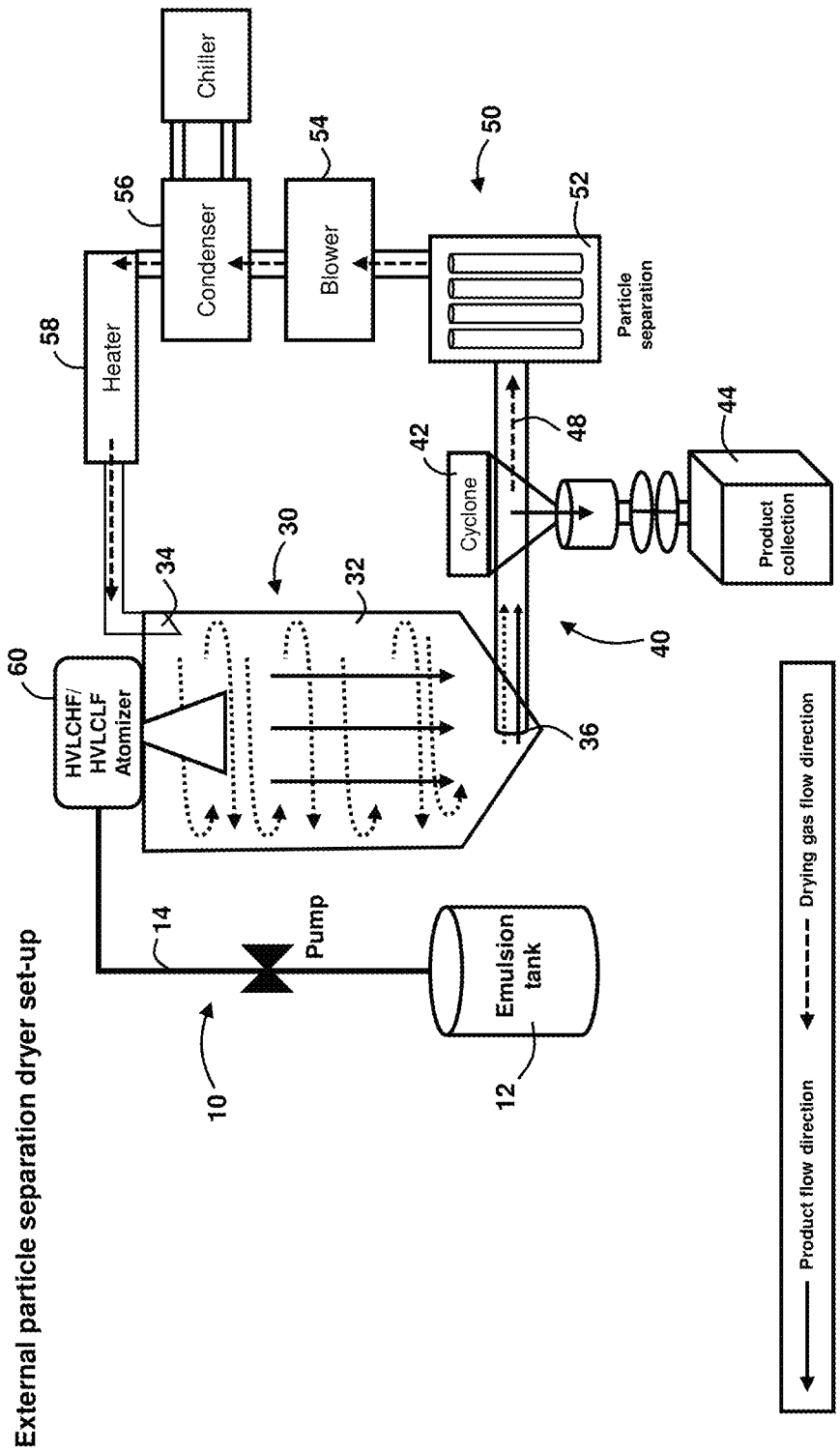

(60) Provisional application No. 62/757,902, filed on Nov. 9, 2018.

(51) Int. Cl.
*B01J 2/04* (2006.01)
*B01J 13/04* (2006.01)

(56) References Cited

U.S. PATENT DOCUMENTS

| | | | |
|---|---|---|---|
| 8,939,388 B1* | 1/2015 | Beetz | B05B 5/03 |
| | | | 239/690 |
| 9,551,527 B2* | 1/2017 | Beetz | A61K 9/16 |
| 10,286,411 B2* | 5/2019 | Ackerman | B05B 7/066 |
| 11,253,833 B2* | 2/2022 | Lagaron Cabello | |
| | | | A61K 9/5063 |
| 2003/0230819 A1* | 12/2003 | Park | A61K 9/5089 |
| | | | 264/4 |
| 2005/0243144 A1* | 11/2005 | Dean | B01J 2/02 |
| | | | 347/74 |
| 2017/0312726 A1* | 11/2017 | Sobel | C11D 3/505 |
| 2019/0336931 A1* | 11/2019 | Lagaron Cabello | B01J 13/043 |

OTHER PUBLICATIONS

Europe Patent Office, Search Report, Application No. 19881780.1-1108/3877081 PCT/US2019059506, mailed Jun. 21, 2022, 9 pages.

* cited by examiner

MICRO ENCAPSULATION USING HIGH-VOLTAGE, LOW-CURRENT, HIGH FREQUENCY ALTERNATING-CURRENT SPRAY ATOMIZATION

BACKGROUND OF THE INVENTION

The present technology relates to a spray drying system and process for encapsulating active ingredients that are volatile, or heat or oxygen sensitive, using spray atomization that applies high-voltage, low-current high frequency alternating-current, or high-voltage, low-current low frequency alternating-current, at the site of atomization. The present technology also relates to the encapsulated product resulting from the spray atomization.

Spray drying systems have been widely utilized in the food and flavor industries to encapsulate food or flavor ingredients, and to transform liquid ingredients into dry flowable powders. Encapsulation is a technique by which a material, or mixture of materials, is coated by another material, or mixture of materials. The coating material is also known as a wall material or a carrier. The wall material forms the outer layer or shell of the encapsulated product. The inner, coated material is known as a core. The spray dried product can be in the form of a core-shell, which contains a single core in the dried particle, or in the form of a matrix, which contains multiple cores in the particle. Since many of the food and flavor ingredients are volatile and chemically unstable in the presence of heat, air, moisture, and/or light, encapsulating these ingredients in a wall material or carrier is a way to limit degradation or loss during processing or storage. The encapsulation process usually requires a heat source to initiate a thermally induced phase separation. The phase separation results in the formation of a surface film or skin layer that permits water to selectively diffuse, while retaining the more volatile components within the core of the encapsulated product.

One disadvantage of conventional spray drying systems for food and flavor encapsulation is the required use of heat energy to induce proper carrier film formation and dehydration in order to obtain a desirable, free-flowing encapsulated powdered product. Typical processing temperatures for conventional spray drying systems range from about 140° C. to about 220° C. for inlet temperatures and 60° C. to 120° C. for outlet temperatures. As a result of such high temperatures, the flavor profile of the dried encapsulated food or flavor component may be significantly different from its original flavor profile, presenting a significant challenge in formulating an acceptable product from highly volatile flavor compounds and heat sensitive food ingredients. Further, the energy and time required to pre-condition the spray dryer to reach the set heating conditions can be costly and time-consuming.

To overcome at least some of the disadvantages resulting from the high temperatures used in spray drying systems, many in the flavor and food industry have developed specific wall materials or carriers to protect against volatilization of the food or flavor components. However, such wall materials or carriers may not be suitable for all types of food or flavor components. In addition, the use of specific wall materials does not address the energy requirements of conventional spray drying systems. Reducing the processing temperatures used in conventional spray drying systems is not a viable solution because, at lower inlet temperatures, such as 120° C., carrier film formation is slower, resulting in higher surface oil content and loss of flavor retention in the resulting product.

One solution to the problem of high temperatures used in conventional spray drying processes is disclosed in Beetz, et al., U.S. Pat. No. 8,939,388. The Beetz et al. approach utilizes a spray drying process in which an electrostatic charge is applied to a high solids, high viscosity emulsion prior to atomization. The electrically charged emulsion is then atomized into electrostatically charged wet particles which are able to be spray dried at lower temperatures.

An electrostatic spray drying process is also disclosed in Sobel et al., U.S. Publication Application No. 2017/0312726A1. In the Sobel et al. process, a liquid emulsion having a viscosity of 150 cP to 250 cP is atomized, an electrostatic charge is applied at the site of atomization, and the atomized emulsion is then dried into an encapsulated free flowing powder. Applying an electrostatic charge at the site of atomization allows the spray drying process to be accomplished at dryer inlet temperatures of about 25° C. to about 110° C.

One disadvantage of electrostatic spray drying processes is the inability to create discrete particles of particular size distributions because of residual static charge. Control over particle size is also limited because the pulse-width of the electrostatic field does not permit complete control. A further disadvantage is that residual static charge build-up can cause product build-up on the walls of the spray dryer and the product conveying systems.

Therefore, a need remains for spray drying systems that mitigate the problems associated with conventional high temperature spray drying systems, while providing an encapsulated product that retains its original flavor profile, and which also provide more control over the particle size and particle morphology of the spray-dried product. There is also a need for an encapsulated product that provides improvements in properties such as encapsulation efficiency, product flowability, and particle size.

BRIEF SUMMARY OF THE INVENTION

One aspect of the present technology is a spray drying process for preparing an encapsulated product, wherein the process facilitates the drying, or desolvating of water, or other appropriate solvent, by applying High-Voltage, Low-Current High Frequency Alternating-Current ("HVLCHFAC"), or "High-Voltage, Low-Current Low Frequency Alternating-Current (HVLCLFAC) to a spray atomizer, or other atomizer, using an electrical resonant transformer (Tesla coil). The process readily converts a liquid emulsion into a free-flowing powder without the need for heat. By administering an HVLCHFAC or HVLCLFAC field about the atomization site, it is possible to reduce the amount of heat energy necessary to facilitate the conversion process of a liquid flavor or food ingredient into a free flowing powder.

In one embodiment, the process comprises the steps of: forming an emulsion by emulsifying at least one core component with a solution or a suspension comprising liquid solvent and at least one wall material; atomizing the emulsion into droplets using an atomizer connected to a high-voltage, low-current high frequency alternating-current source or a high-voltage, low-current low frequency alternating-current source; drying the droplets in a dryer chamber at an inlet temperature of about 25° C. to about 150° C. and an outlet temperature of about 25° C. to about 110° C. to obtain the encapsulated product. In some embodiments, higher inlet temperatures can be employed, ranging from greater than 100° C. to about 150° C.

In another aspect, the present technology provides a spray drying system that includes an atomizer for atomizing the emulsion into droplets and a dryer for drying the atomized droplets. An electrical resonant transformer is connected to the atomizer and applies a high-voltage, low-current high frequency alternating-current, or a high-voltage, low-current low frequency alternating-current, at the site of atomization. The alternating current applies energy to the emulsion being atomized, enabling lower temperatures to be used for the drying gas in the dryer, compared to conventional spray drying systems. An inert gas can be used in the spray drying system to enhance the product quality attributes of the finished powders. The inert gas can be used as a fluid for atomization and as a drying gas within the drying chamber of the spray dryer.

In a further aspect, the present technology provides an encapsulated product prepared by spray drying a liquid emulsion comprising at least one core component and at least one wall material, wherein an electric charge from a high-voltage, low-current alternating-current source is applied to the liquid emulsion. The encapsulated product can have a core-shell structure or a matrix structure. In some embodiments, the high-voltage alternating-current can act as a bactericide, thereby improving food safety.

At least one aspect of the presently described technology provides encapsulated food and flavor products having improved quality characteristics, such as increased encapsulation efficiency (ingredient retention) and/or a flavor profile comparable to that of the starting food or flavor ingredient. By mitigating problems associated with conventional high-temperature spray drying, the present technology produces a free-flowing, encapsulated powder that retains its original flavor profile. In addition, in some embodiments, the encapsulated food and flavor products can have improved shelf-life compared to conventional and electrostatic spray-dried products due to the bactericidal properties imparted by the high-voltage alternating-current source.

Further details and embodiments are disclosed in the discussion of the detailed description below.

BRIEF DESCRIPTION OF THE DRAWINGS

FIG. 1 is a schematic of one embodiment of a spray drying system of the present technology;

FIG. 2 is a cross-sectional view of one embodiment of a spray nozzle used in the spray drying system of the present technology;

FIG. 3 is a cross-sectional view of an alternative embodiment of a spray nozzle used in the spray drying system of the present technology;

FIG. 4 is a cross-sectional view of another alternative embodiment of a spray nozzle used in the spray drying system of the present technology;

FIG. 5 is a schematic of an alternative embodiment of a spray drying system of the present technology;

FIG. 6 is a schematic of an alternative embodiment of a spray drying system of the present technology;

FIG. 7 is an SEM photograph showing the morphological characteristics of a control sample 1 encapsulated product.

FIG. 8 is an SEM photograph showing the morphological characteristics of the encapsulated product made in Example 1.

FIG. 9 is an SEM photograph showing the morphological characteristics of the encapsulated product made in Example 2.

FIG. 10 is an SEM photograph showing the morphological characteristics of the encapsulated product made in Example 3.

FIG. 11 is an SEM photograph showing the morphological characteristics of the encapsulated product made in Example 4.

FIG. 12 is an SEM photograph showing the morphological characteristics of the encapsulated product made in Example 5.

FIG. 13 is an SEM photograph showing the morphological characteristics of the encapsulated product made in Example 6.

FIG. 14 is an SEM photograph showing the morphological characteristics of the encapsulated product made in Example 7.

FIG. 15 is an SEM photograph showing the morphological characteristics of the encapsulated product made in Example 8.

DETAILED DESCRIPTION OF THE INVENTION

The presently described technology provides an improved spray drying system and method for preparing an encapsulated product comprising at least one core component and at least one carrier or wall material. The method comprises atomizing an emulsion formed from the core material and the carrier or wall material, and applying a high-voltage, low-current high frequency alternating-current (HVLCHFAC) or a high-voltage, low-current low frequency alternating-current (HVLCLFAC) at the site of the atomization. The HVLCHFAC/HVLCLFAC field applied to the atomized emulsion facilitates film formation by the wall material, without the high heat typically required to induce film formation. As a result, the emulsion can be dried with mild or no heat being supplied to the drying chamber to produce an encapsulated spray-dried powder.

The encapsulated product of the present technology is prepared from a formulation comprising a solids component and a liquid solvent component. The solids component comprises from 45% to 95%, alternatively from 50% to 90%, alternatively from 60% to 85%, alternatively from 75% to 85% by weight of at least one carrier or wall material, and from 5% to 50%, alternatively from 10% to 50%, alternatively from 15% to 40%, and alternatively from 15% to about 25%, by weight of at least one core material. The carrier or wall material is selected from a variety of materials or mixtures thereof, including carbohydrates, proteins, gums, lipids, waxes, food grade polymers, phospholipids, cellulosic materials, and cell materials, including but not limited to yeast cells or cell wall materials. Desirable wall materials should have GRAS (generally recognized as safe) status, have film-forming capacity, be capable of forming a stable emulsion with the core material, and be non-reactive with the core material.

Examples of suitable carbohydrates for use as a carrier or wall material include maltodextrin, chitosan, sucrose, glucose, lactose, dextran, corn syrup, cyclodextrin, isomalt, amylose, modified food starch, sugar-based material, sugar alcohol-based material, and mixtures thereof. Examples of suitable protein materials include gelatins, soy proteins, whey proteins, zein, casein, albumin, hemoglobin, peptides, gluten, and mixtures thereof. Examples of suitable gums include gum arabic, gum acacia, agar, sodium alginate, carrageenan, xanthan gum, gelatins, and mixtures thereof. Examples of suitable cellulose materials include carboxymethyl cellulose, methyl cellulose, ethyl cellulose, nitrocellulose, acetylcellulose, cellulose acetate-phthalate, cellulose acetate-butyrate phthalate, and mixtures thereof. Selection of the carrier or wall material will depend upon the core material and the requirements for the encapsulated product.

The core material can include any natural or created flavor base oil, for example, citrus, spice, mint, berry, tropical fruit or savory types, or essential oils. The core material can also include individual components of any of the natural or created oils or flavors, such as, for example, benzaldehyde, isoamyl acetate, ethyl butyrate, linalool, methyl salicylate, limonene, menthol, decanol, diethyl phthalate, and citral. The base oil may contain several flavor/aroma compounds, depending on the type of flavor creation. The core material can also be other natural or synthetic materials that can benefit from encapsulation. Such other materials include, for example, animal and/or vegetable oils, animal and/or vegetable protein, starch and starch derivatives, coffee, tea, vegetable or fruit juices, milk protein fractions, eggs, cereal, stevia, animal feed, cocoa powder, vitamins, nutraceuticals, coloring agents, perfumes, fragrances, spices, flavorings, enzymes, pharmaceutical actives, agricultural actives, including fertilizers and pesticides, pharmaceutically or nutritionally acceptable salts, ceramic materials, catalyst supports, microalgae, and hemoglobin. The core material can also comprise mixtures of the foregoing core materials.

The formulation may include one or more optional additives, such as, for example, emulsifiers, antioxidants, colorings, sweeteners, animal/vegetable oil, animal/vegetable protein, food acids, salts, diluents, flavor maskers, flavor enhancers, fillers, preservatives, fruit/vegetable extracts, stabilizers, lubricants, and the like. Such additives are known to one of skill in the art. Examples of emulsifiers that can be used include monoglycerides, mono- and diglyceride blends, propylene glycol monoglycerides, lecithin, modified lecithins, acetylated monoglycerides, lactylated fatty acid esters of glycerol and propylene glycol, lactylated propyleneglycol monoglycerides, sorbitan esters, sorbitan-polyoxyethylene [20] monoglycerides, polyglycerol esters, diacetyltartarate esters of monoglycerides (DATEMs), succinylated esters of monoglycerides, polyoxyethylenepropylene copolymers, ethylene oxide-propylene oxide copolymers, and mixtures thereof. Examples of suitable antioxidants include rosemary oil and Vitamin E. Typical amounts of additives, when employed, can range from about 0.1% to about 10% by weight for emulsifiers, from about 0.01% to about 5% by weight for antioxidants, and about 0.01% to about 10% for other additives.

The liquid solvent component of the spray dry formulation is usually water, but other suitable solvents, such as hexane or ethanol or a combination of solvents could be used. The choice of liquid solvent will depend on the solids component and the end use for the spray dried product.

The spray dry formulation is prepared by emulsifying together the liquid solvent, the wall material and the core material, and any optional components, to form an emulsion. In some embodiments, the wall material is pre-hydrated in water prior to the emulsification with the core material. The wall material can be supplied from the manufacturer in pre-hydrated form, or hydrated in water prior to use. Better flavor retention is achieved when the wall material is extensively solubilized and/or fully saturated prior to emulsification. The amount of water and hydration time needed to saturate the wall material will depend upon the type of wall material used in the formulation. For example, some starches may need to be hydrated overnight in order to avoid residual granules and fully perform the function of an interface between the water and flavor component (oil) in the emulsion. Preferably, sufficient water is used to form an aqueous solution or suspension of the wall material.

Emulsification of the core material with the wall material and liquid solvent can be accomplished by using a high shear mixer or a homogenizer. In general, higher shear rates tend to produce better, more homogenous emulsions having smaller micelles. Suitable devices for achieving a high shear rate include but are not limited to an HSM-100-LSK high shear mixer, available from Ross, operated for 5 to 20 minutes at 2,000 rpm to 10,000 rpm, or a homogenizer available from Nano Debee, operated at a pressure of 2,000 psi to 60,000 psi through 2 to 6 cycles. It should be appreciated that these devices are only exemplary, and that other suitable devices can be determined by one of skill in the art. The specific equipment and operating conditions employed to obtain a liquid emulsion will depend, at least in part, upon the core and wall materials selected. The resulting emulsion has a viscosity suitable for pumping and atomizing the emulsion in a spray drying system. Viscosities can range from about 50 cP to about 10,000 cP, alternatively about 100 cP to about 7,000 cP, alternatively about 150 cP to about 4,000 cP, alternatively about 150 cP to about 1,500 cP, alternatively about 150 cP to about 600 cP, to about 700 cP, to about 800 cP, to about 900 cP, or to about 1,000 cP. The resulting emulsion has a solids content, comprising the wall material, the core material, and any additives that ranges from about 15% to about 70% by weight of the emulsion, alternatively from about 15% to about 65%, to about 60%, to about 55%, to about 50%, or to about 45% by weight of the emulsion.

Figure 2:
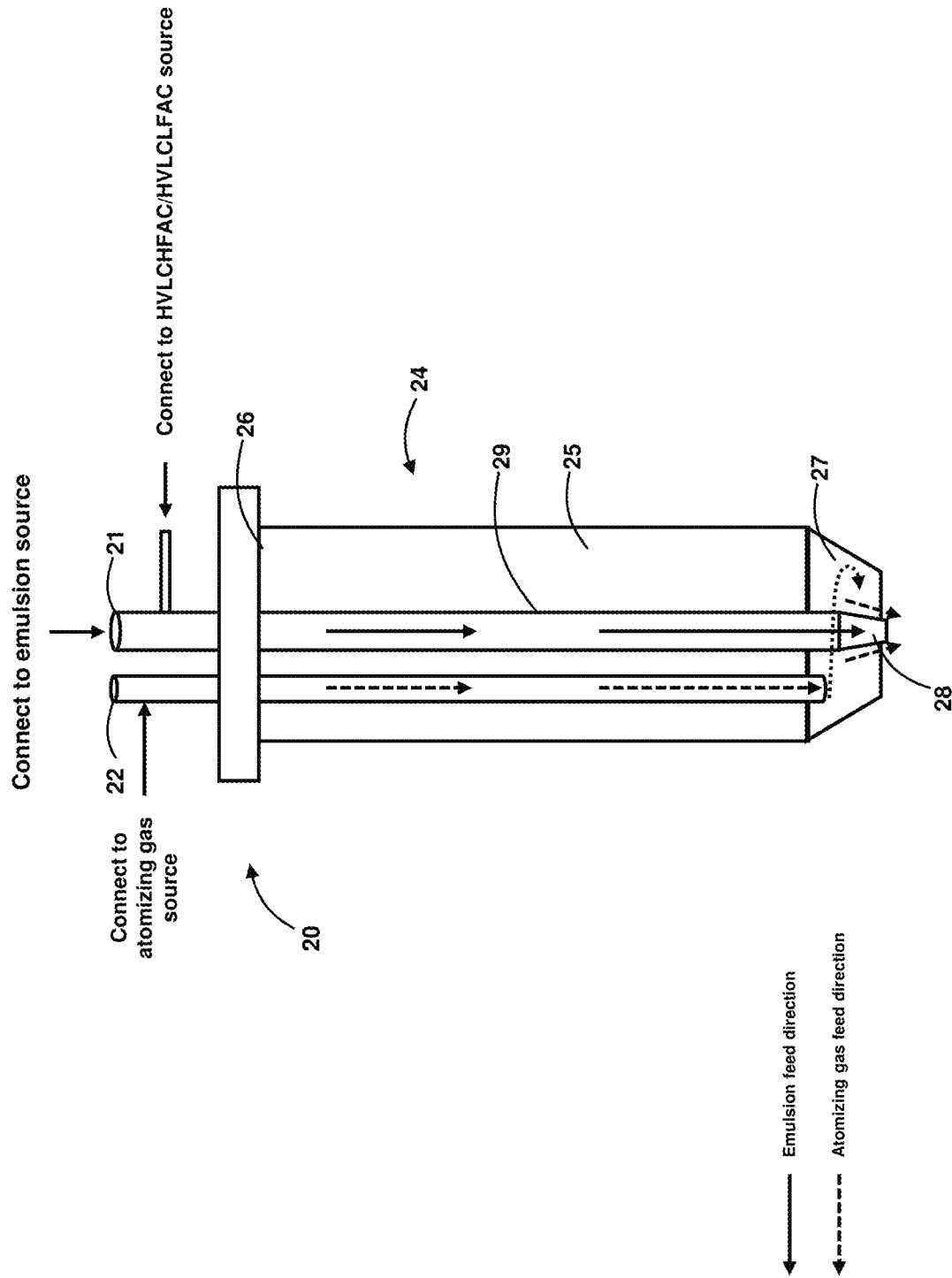

Once the emulsion of the core material and the wall material has been prepared, it is introduced into the spray drying system, where the liquid emulsion is dried into a free-flowing powder of encapsulated core material. One embodiment of the spray drying system is shown in FIG. 1. The spray drying system 10 comprises an atomizing unit 20 for atomizing the emulsion into droplets, a drying unit 30 connected to the atomizing unit, for drying the droplets into a powder, and a collection unit 40 for collecting the dried powder product. The spray drying system may also include a recirculation unit 50 that allows drying gas exiting from the drying unit to be processed and reused in the drying unit. Referring to FIGS. 1 and 2, each of the units will now be described in further detail.

The atomizing unit 20 includes an inlet port 21 for receiving the emulsion to be dried. Typically, the emulsion is mixed and/or stored in an emulsion tank 12 and is pumped via a feed pump 14 to the inlet port 21 of the atomizing unit 20. Any suitable feed pump 14 can be used to pump the liquid emulsion into the atomizer unit. The feed rate for pumping the liquid emulsion will depend, at least in part, on the scale of the spray drying system, and can range from about 5 ml/min to about 15 ml/min for bench scale operations, to about 500 ml/min to about 10,000 ml/min for production scale operations. In one embodiment, the feed rate can range from about 5 ml/min to about 500 ml/min.

The atomizing unit 20 can include a number of different atomizers known in the art, such as, but not limited to, a dual-fluid nozzle, a rotary atomizer nozzle, a pressurized nozzle, or other commercially available atomizing nozzle. In one embodiment, the atomizing unit comprises a dual-fluid spray nozzle 24, shown in FIG. 2. The spray nozzle 24 includes an elongated body 25 having a proximal end 26 connected to the inlet port 21, and a downstream or distal end 27, which has a spray tip 28. A hollow conductive metal electrode 29 extends through the body 25, from the inlet port to the spray tip 28, and receives and conveys the emulsion to be atomized. A high voltage alternating current source 60 is connected to a proximal end of the conductive metal electrode 29, and imparts a charge to the emulsion as the emulsion travels through the electrode to the spray tip 28.

An important aspect of the present technology is the use of a high-voltage, low-current high frequency alternating-current source, or alternatively a high-voltage, low-current low frequency alternating-current source, to impart an alternating-current charge to the emulsion. By "high voltage" is meant a voltage of at least 2 kVAC, preferably at least 10 kVAC and can range up to 200 kVAC or more. In one embodiment, the high-voltage source 60 supplies a voltage ranging from about 20 kVAC to about 50 kVAC. By "low current" is meant a current that is less than 1 mA. The frequency of the current source can range from about 50 kHz to 30 Mega hertz (MHz), depending on whether the alternating-current source is a high frequency or low frequency current source. Low frequency can range from about 50 kHz to about 3 MHz. High frequency can range from about 3 MHz to about 30 MHz. Without being bound by theory, the alternating-current provides a localized charge at the surface of the atomized droplet which can result in faster skin formation compared to an electrostatic charge provided by a direct current. Faster skin formation can lead to better encapsulation efficiency and less loss of volatile components. The alternating-current provides neutral charged droplets that do not exhibit a build-up of static charge. This can reduce the amount of product build-up on the spray dryer walls that can occur in electrostatic spray drying systems due to residual static charge build-up. The alternating-current also allows better control of the particle size and particle morphology compared to conventional and electrostatic spray drying systems.

The high-voltage, low-current alternating-current source is an electrical resonant transformer circuit (Tesla coil). A Tesla coil is a high frequency oscillator that drives a tuned resonant air core transformer to convert low-voltage high current to high-voltage low current. The alternating current produces frequencies in the low radio frequency range, about 50 kHz to about 1 MHz, and is dependent upon the capacitance frequency. Higher frequencies can be obtained by changing the capacitance and/or spark gap distance within the tank circuit of a spark gap-type Tesla coil, or by triggering high speed switching transistors in a solid state-type Tesla coil. There are three types of Tesla coils: spark excited or spark gap Tesla coil, switched or solid state Tesla coil, and continuous wave Tesla coil. Spark gap Tesla coils utilize a spark gap to switch oscillating current between primary and secondary circuits. Spark gap Tesla coils can be stationary spark gap, stationary triggered spark gap, or rotary spark gap. Solid state Tesla coils use semiconductor devices to switch pulses of current from a DC power supply through the primary circuit. The pulses of current to the primary circuit excite resonance in the secondary tuned circuit. Solid state Tesla coils can be single resonant solid state Tesla coils or dual resonant solid state Tesla coils. Continuous wave coils generate a continuous sine wave output rather than a pulsed output. Although it is contemplated that any of the three types of Tesla coils could be used in the present technology, a switched or solid state Tesla coil is preferred for safety reasons.

The atomizing unit 20 also includes a gas inlet port 22 for introducing an atomizing gas into the spray nozzle. The atomizing gas can be delivered through the gas inlet port 22 at a pressure of about 5 psi to about 120 psi, alternatively about 20 psi to about 80 psi, alternatively about 40 psi to about 60 psi. In some embodiments, the atomizing gas supplied to the spray nozzle can be heated. Temperatures for the atomizing gas can range from ambient temperature to about 130° C. In some preferred embodiments, the temperature of the atomizing gas is in the range of about 60° C. to about 90° C. By heating the atomizing gas, thermally induced phase separation of the liquid and solids in the emulsion happens faster than if the atomizing gas is at ambient temperature, resulting in faster film formation by the wall material at the droplet surface. In some alternative embodiments, the atomizing gas can be cooled prior to delivery to the spray nozzle, such that the gas is at a temperature below ambient.

The atomizing gas can be air, carbon dioxide, or an inert gas, such as nitrogen, argon, helium, xenon, krypton, or neon, although nitrogen is preferred. Use of an inert gas, such as nitrogen, as the atomizing gas also offers the benefit of reducing the concentration of oxidative by-products in the finished encapsulated powdered product that otherwise could occur if air were used as the atomizing gas. As a result, the encapsulated powdered product has better flavor and/or color due to lower concentrations of oxidative degradation products. An inert gas also enhances a safety aspect of the spray dry system since the nozzle tip can emit sparks capable of igniting flammable materials and powders. Accordingly, in some embodiments, the atomizing gas does not include air.

The atomizing gas and the emulsion travel in co-current flow through the hollow electrode 29, and meet at the tip 28 of the electrode. The emulsion becomes charged while going through the conductive electrode due to the high voltage charge being supplied by the high voltage alternating current source 60. The charged emulsion is atomized by the tangential shearing forces provided by the pressurized gas at the tip 28 of the electrode and sprayed into the drying unit 30. Without being bound by theory, it is believed that the HVLCHFAC field, or HVLCLFAC field, applied to the emulsion at the site of atomization drives the core material into the center of the atomized droplet and facilitates film formation by the wall material at the droplet surface. Since film formation is accomplished through application of the electric field, the high temperatures required for proper film formation in conventional spray drying systems can be avoided, allowing significantly reduced drying temperatures to be used in the present system. In addition, the atomized cloud of droplets acts as a capacitor (stray capacitance) and can interact with the ground, thereby facilitating the low temperature drying. In some embodiments, the electrical resonant transformer circuit which supplies the high-voltage, low-current alternating-current can be tuned for resonance with the capacitance developed in the atomized cloud of droplets. Tuning the alternating-current waveform frequency to match the inductance and capacitance of the droplet cloud brings the system into resonance, and provides the maximum amount of charge for drying, thereby improving efficiency of the drying system.

Figure 3:
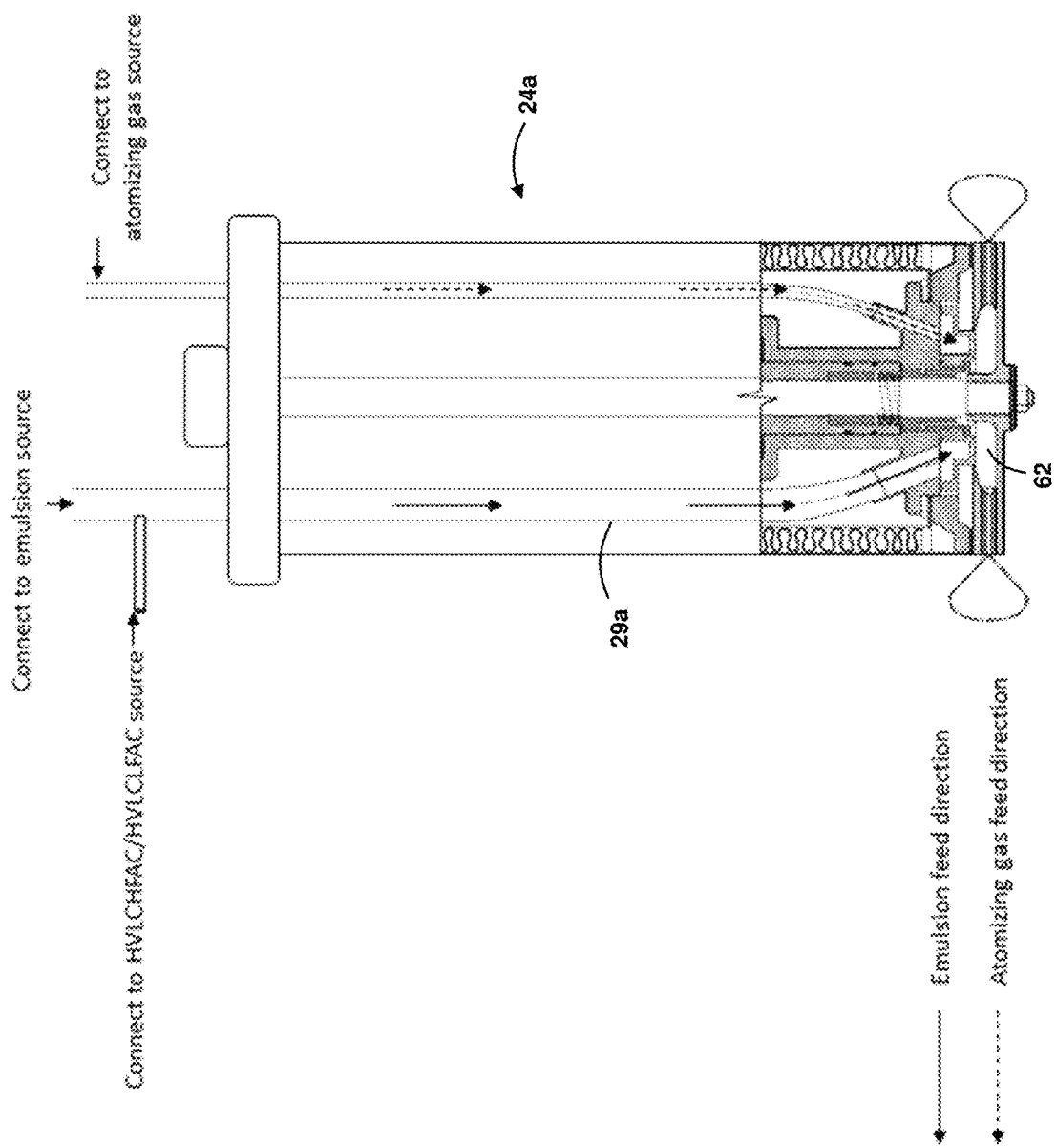

In an alternative embodiment, a rotary atomizer nozzle, such as shown in FIG. 3 as 24*a*, can be used for atomizing the emulsion into droplets. The rotary atomizer nozzle 24*a* employs a spinning disc or plate 62, instead of a spray tip to atomize the emulsion into droplets. Like the dual-fluid nozzle shown in FIG. 2, the rotary atomizer nozzle 24*a* includes a hollow metal electrode 29*a* connected to a high-voltage alternating-current source. The high-voltage, alternating-current source imparts an alternating current charge to the emulsion as the emulsion travels through the electrode 29*a* to the plate 62.

Figure 4:
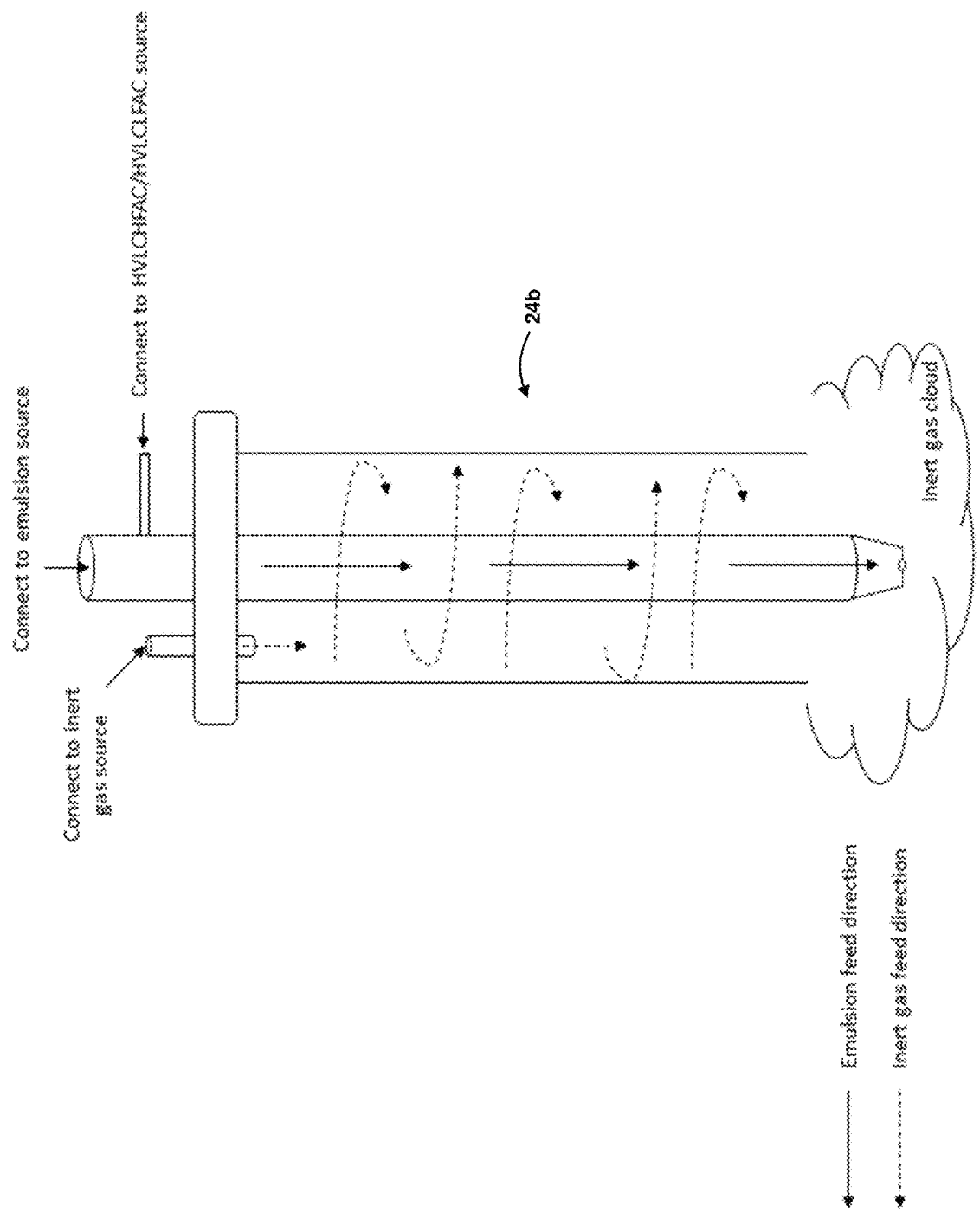
Figure 5:
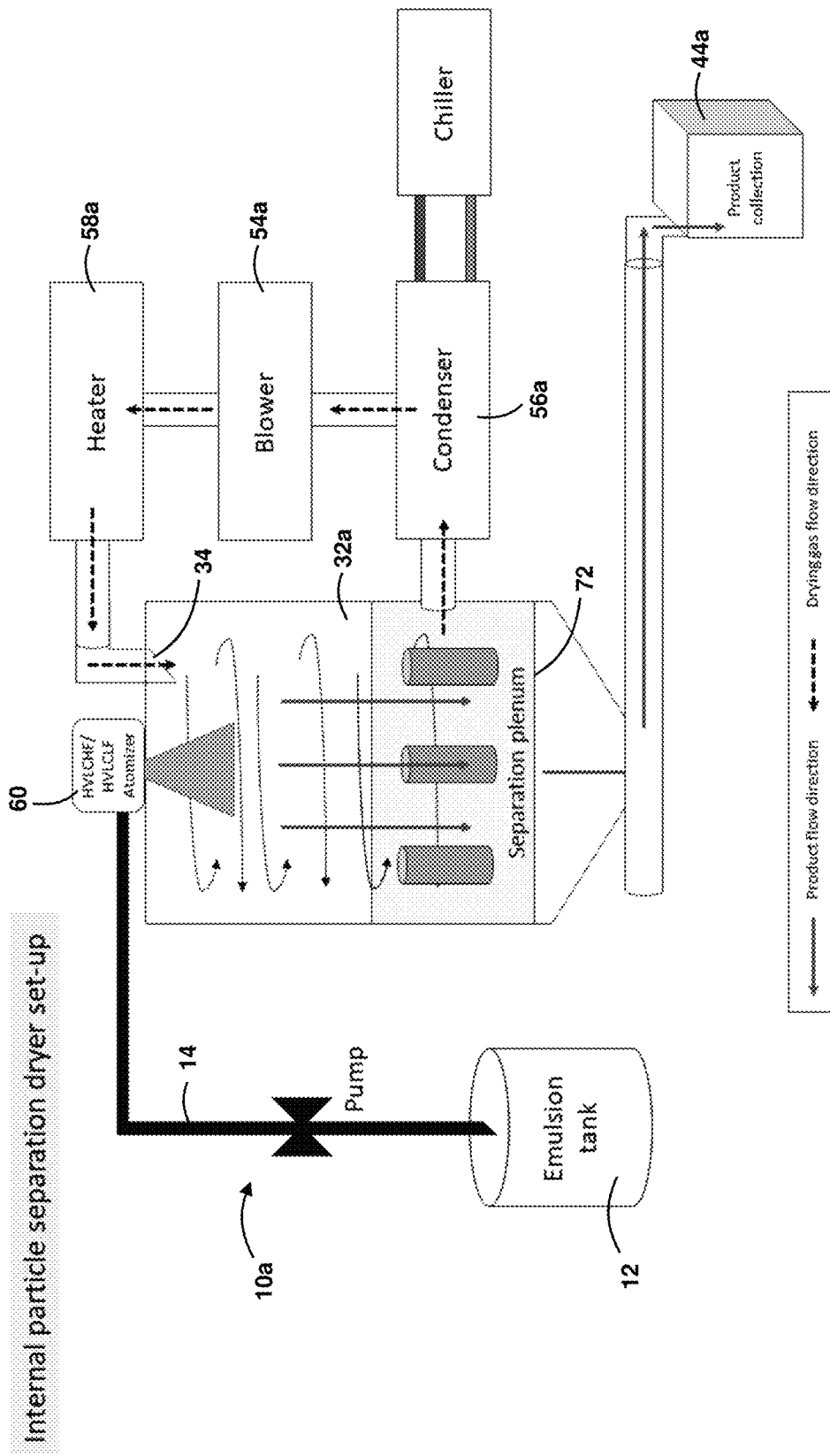
Figure 6:
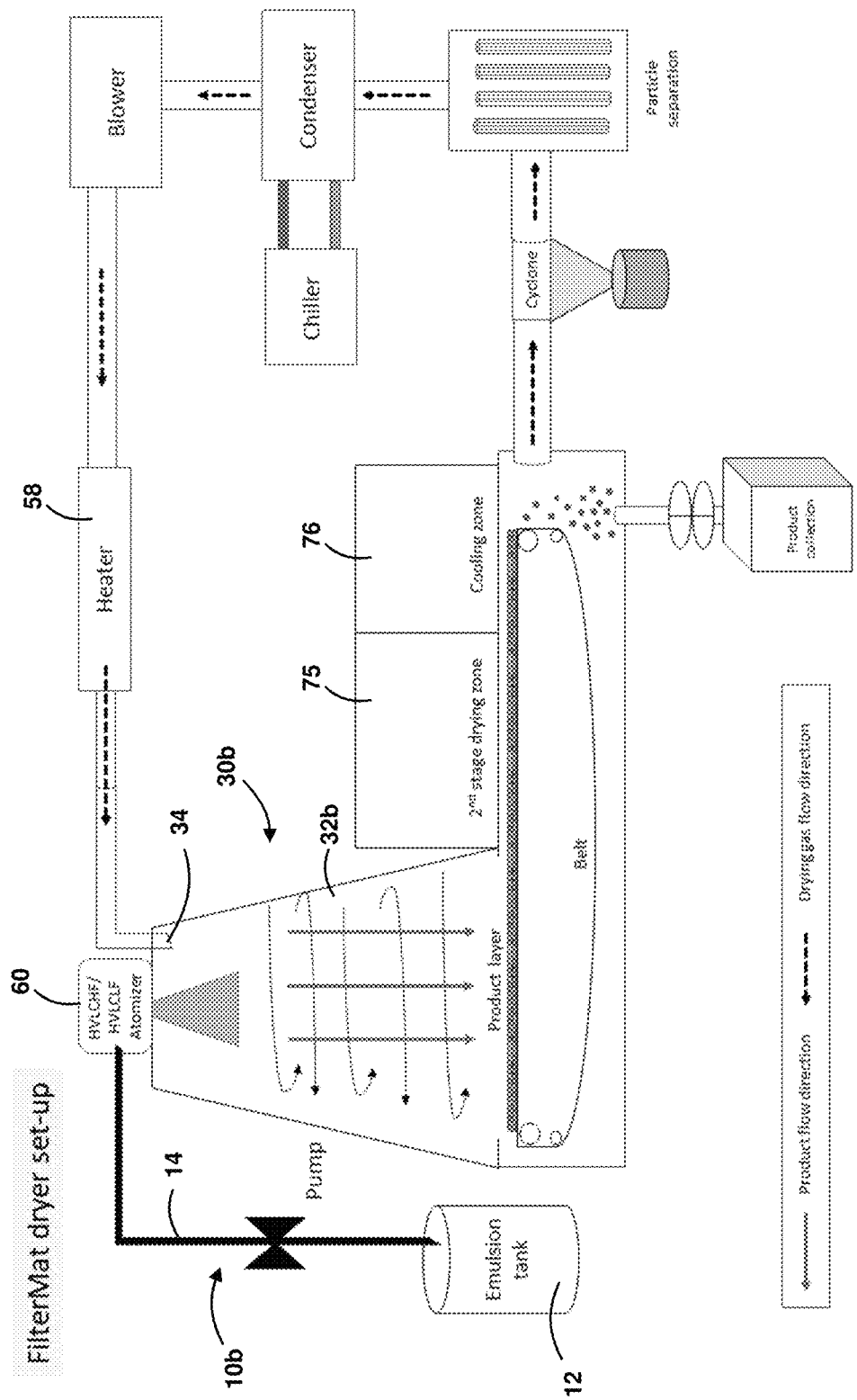

In a further embodiment, a pressurized nozzle, such as shown in FIG. 4 as 24*b*, can be used for atomizing the emulsion into droplets. Regardless of the atomizer employed, a high-voltage, alternating-current source is connected to the conductive metal electrode within the atomizer nozzle, and imparts an alternating current charge to the emulsion as the emulsion travels through the electrode and is sprayed into the drying unit.

Referring again to FIG. 1, the drying unit 30 comprises a drying chamber 32 for drying the atomized emulsion droplets, a dryer inlet 34 for receiving the drying gas, and a dryer outlet 36 through which the dried encapsulated product and drying gas exit the drying chamber. Inside the drying chamber, the dryer inlet temperature can range from 25° C. to 150° C., and the dryer outlet temperature can range from 25° C. to 110° C. These temperatures are significantly lower than the processing temperatures of conventional spray drying systems. The drying gas can be a mixture of inert gas and air, so that the oxygen concentration of the drying gas stream is lower than air. Preferably, the oxygen concentration of the drying gas is lower than 5% by volume. In some embodiments, nitrogen gas, used as the atomizing gas, enters the drying chamber through the atomizer, and mixes with the gas in the drying chamber to maintain the oxygen concentration at less than 5% by volume. Alternatively, nitrogen gas could be introduced through a port in the drying chamber to maintain the oxygen concentration at less than 5%.

The drying gas flowing within the drying chamber 32 contacts the atomized droplets and evaporates the water. The gas flow can be either co-current or counter-current to the flow of atomized droplets. The gas flow rate will depend on the size of the drying unit, but can range from about 150 standard cubic feet per minute (scfm) to about 18,000 scfm, alternatively about 500 scfm to about 15,000 scfm, alternatively about 700 scfm to about 10,000 scfm.

The drying gas conveys the dried, encapsulated product from the drying chamber into the product collection unit 40 where it is collected as a final product. The product collection unit comprises a separation cyclone 42, where the dried particles are separated from the drying gas, and a product collection chamber 44 which receives the final encapsulated product. The drying gas exits the separation cyclone as exhaust gas through an exhaust outlet 48.

In a preferred embodiment, the exhaust outlet 48 is coupled to the recirculation unit 50 so that the exhaust gas can be processed and recirculated into the drying chamber. In the recirculation unit, the exhaust gas is filtered through a particle separator 52, and then conveyed by a blower 54 to a condenser 56. The condenser 56 removes excess moisture from the exhaust gas, typically by means of cold water condensing coils. Preferably as much moisture as possible is removed from the exhaust gas so that the moisture level in the recirculated gas is less than 10%, preferably less than 3%. The dried gas is directed by the blower 54 through a heater 58, which reheats the gas to an appropriate temperature for reuse as the drying gas. The recirculated drying gas mixes with nitrogen gas introduced through the atomizer, or an alternative port in the drying chamber, to maintain the oxygen content of the drying gas below 5%.

The present technology could be used in a variety of types of commercially available spray dryers or fluidized bed spray dryers with modification of recycling of the drying gas. Types of spray dryers include, but are not limited to, a conventional spray drying system having an external particle separation set-up, such as shown in FIG. 1. In an alternative embodiment, the spray drying system could comprise a modified spray dryer system **10*a* having an internal particle separation set-up, as shown in FIG. 5. The system shown in FIG. 5, where like numerals represent like parts, is similar to that shown in FIG. 1. Instead of the separation cyclone 42, shown in FIG. 1, the system shown in FIG. 5 employs a separation plenum 72 within the drying chamber 32*a* to separate the dried particles from the drying gas. A product collection chamber 44*a* receives the final dried encapsulated product. The drying gas exits the drying chamber 32*a* as exhaust gas and travels through a condenser 56*a*, where any water vapor is removed from the exhaust gas, typically by means of cold water condensing coils. The dried exhaust gas is then directed by a blower 54*a* through a gas heater 58*a*** which reheats the drying gas to an appropriate temperature for reuse as the drying gas. The recirculated drying gas then mixes with nitrogen gas introduced through the atomizer, or an alternative port in the drying chamber, to maintain the oxygen content of the drying gas below 5%.

As a further alternative, the spray drying system could be a modified spray drying system **10*b* shown in FIG. 6. This system employs a FilterMat spray dryer set-up, which equips the drying unit 30*b* with a drying chamber 32*b*, a secondary drying zone 75 and a cooling zone 76, as shown in FIG. 6**. It is also contemplated that the present technology could be used with other types of fluidized dryers.

The present technology provides several advantages over traditional spray dry technologies. Traditional spray drying operates at high temperatures ranging from about 150° C. to about 210° C. for the inlet temperatures and about 60° C. to about 120° C. for the outlet temperature. Such temperatures require 30 to 50 minutes pre-condition time for the spray dryer to reach the set heating conditions. During the typical spray dry process, the product that is stuck in the drying chamber will not be collected because of long exposure in the heat abusive environment, thus leading to product yield ranges that are only from 60 to 90%. As a result of the heat-abusive processing, much of the highly volatile components are volatized off, which reduces encapsulation efficiency by 15 to 20%. The products resulting from a conventional spray dry process are usually in the form of a free-flowing powder, with particle sizes ranging from 80-350 μm. The product may have odors due to un-encapsulated surface flavor that brings concern of cross-contamination for certain food production. The encapsulated spray dried flavor is widely applied in variety of food and beverages products. However, the common challenges of using spray dried flavor are issues of dust during food processing, floating and slow hydration in water-based applications.

Because of the lower processing temperatures used in the present technology, the time required for pre-conditioning the spray dryer is reduced significantly to 5 to 30 minutes, and less energy consumption is required, depending on dryer capacity. A further advantage of the low processing temperatures is that the dried product remaining in the drying chamber has a quality comparable to that of the product collected from the product collection chamber. Consequently, the product in the drying chamber can also be collected, increasing the product yield to above 90%. In terms of product quality, the process of the present technology provides superior retention of volatile flavor components, thus making the flavor profile of the product closer to that of the original created flavor formulation. The product of the present technology also has less surface oil than conventional spray dried products, which can lead to a more shelf-stable product since surface oil oxidation is minimized. In conventional spray dried products, surface oil content is typically 1% to 5%. The product of the present technology, however, is able to achieve a surface oil amount of less than about 1%, preferably less than about 0.5%, more preferably about 0.4% or less, based on the total weight of the product. In some embodiments, the product of the present technology has an amount of surface oil as low as 0.01% by weight. The process of the present technology also offers a product with less head-space aroma due to low surface flavors, thereby eliminating flavor cross-contamination. The process also provides better control over the particle size and particle morphology than conventional or electrostatic spray drying systems, resulting in products that can have a designed particle size range. In some embodiments, the process of the present technology can provide products with larger particle sizes than conventional spray drying processes. The larger particle sizes can range from about 80 µm to about 600 µm, which can potentially resolve dusting issues and offer great instant hydration properties in water-based applications. In some embodiments, the spray dried products have a particle size distribution wherein the median or D50 value is at least 85 µm, compared to a D50 value of less than 50 µm for conventional spray dried products. In other embodiments, the D50 value of the spray dried powder of the present technology is at least 75 µm. Depending on the type of product, it may be desirable to have small particle sizes, such as in the range of less than 1 µm to about 300 µm, alternatively less than 1 µm to about 250 µm, with a D50 value of less than 40 µm. The process of the present technology can achieve such small particle sizes by utilizing an emulsion having a solids content of less than 50% by weight. In some embodiments, the spray dried products have an agglomerated morphology, with multiple smaller particles adhered to larger particles forming agglomerates. In other embodiments, the process can be adjusted to deliver a discrete particle morphology. It is also contemplated that, in some embodiments, the high-voltage alternating-current used in the present technology acts as a bactericide, killing bacteria and/or other microbes and thereby improving food safety.

The preceding embodiments are illustrated by the following examples, which are not to be construed as limiting the invention or scope of the specific procedures or formulations described herein. One skilled in the art will recognize that modifications may be made in the presently described technology without deviating from the spirit or scope of the invention.

Example 1-2

Materials and Methods

An example formulation was prepared to evaluate the effects of the low temperature spray dry process of the present technology compared to a conventional, high temperature spray dry process. The formulation contained 80 parts by weight of OSAN-starch (Hi-Cap™ 100, National starch and Chemical Co.) as the carrier material, and 20 parts by weight of orange oil (FONA, Inc. 1-fold orange oil 160.1515) as the core material. The water used to hydrate the carrier was 82 parts so that the example emulsion contained about 55% by weight solids. The emulsion was prepared by emulsifying the orange oil with pre-hydrated OSAN-starch (Hi-Cap™ 100) by using a high shear mixer (Charles Ross & Son company, Model: HSM-100LSK, Ser #: 205756) at 5,000 rpm for 5 minutes. After high shear mixing, the mixture was homogenized using a homogenizer (Gaulin Corporation, Type 405M3 3TPS) with a first pass at 3,000 psi and a second pass at 500 psi.

Sample Made by Conventional Spray Dry (Control Sample 1)

An emulsion made by the process as described above was sprayed into a pilot size spray dryer with an emulsion feed rate at 180 ml/minute, air pressure at 40 psi, and drying gas flow at about 50 scfm. The dryer temperature was set at 190° C. for the inlet and 90° C. for the outlet. The product was collected as a free-flowing dry powder from the product collector for further evaluation.

Sample Made by the Present Technology (Examples 1 & 2)

An emulsion made by the process described above was sprayed into a pilot dryer with the function of drying gas recycle. The HVLCHFAC spray nozzle was charged with 20 kVAC for Example 1 and 50 kVAC for Example 2. Emulsion feeding rate was set at 0.4 lbs/minute with air pressure at 60 psi and airflow rate at 650 scfm. The inlet temperature for both Example 1 and 2 was set at 90° C. and the outlet temperature was observed at around 50° C. The final products were collected as free-flowing dry powder.

TABLE 1

Processing Parameters and Observations

|  | Control 1 | Example #1 | Example #2 |
|---|---|---|---|
| Processing parameter: | | | |
| Spraying nozzle | | | |
|  | Standard dual-fluid nozzle | HVLCHFAC spray nozzle 20 kVAC charged | HVLCHFAC spray nozzle 50 kVAC charged |
| Emulsion solid content (%) | 55 | 55 | 55 |
| Inlet temperature (° C.) | 190 | 90 | 90 |
| Outlet temperature (° C.) | 85-90 | 50 | 50 |
| Delivering gas | Air | Nitrogen | Nitrogen |
| Emulsion feeding rate (ml/min) | 180 | 180 | 180 |
| Atomizing gas pressure (psi) | 40 | 60 | 60 |
| Atomizing gas temperature (° C.) | 25 | 90 | 90 |
| Visual appearance of final product | Free flowing powder | Free flowing powder | Free flowing powder |

The product quality was evaluated in total oil, surface oil, moisture content and surface morphology.

Total Oil Analysis:

The total oil content was determined by a Clevenger apparatus. Ten grams of product powder were dissolved in 150 ml of water in a 500 ml round bottom flask. An appropriate amount of boiling chips and antifoaming agent were added into the solution. The Clevenger apparatus was fitted onto the top of the flask with a water-cooled condenser device. The solution was distilled for 3 hours. The total oil content was calculated by the weight of recovered oil divided by the total sample weight, as shown in the following equation. Each example was performed in triplicate.

Total Oil (%) = (Recovered Orange Oil weight/Sample weight) × 100(%)

Surface Oil Analysis:

The surface oil is determined by gravimetric mean. The dry powder sample (10 g) was mixed with 150 ml n-pentane for 4 hours. The surface oil is extracted in the solvent phase. The solvent was separated from the dry powder by filtration and dried by nitrogen gas in a flask. The amount of surface oil was determined by the flask weight (after solvent evaporation) minus the original weight of the flask as shown in the following equation. Each example was performed in triplicate.

Surface Oil (%) =

(Container wt. after pentane evaporation−container wt./Sample weight) ×

100(%)

Encapsulation Efficiency:

Encapsulation efficiency is calculated by using the following equation:

$$\text{Encapsulation Efficiency} = \frac{\text{Total Oil Content (per g of sample)} - \text{Surface Oil Content (per g of sample)}}{\text{Original Oil Wt/Carrier Wt}}$$

Particle Size Analysis:

The particle size of the sample was measured by using a laser diffraction particle size analyzer (Beckman Coulter, LS 13 320). The D50 value was calculated and used to compare the particle size between each sample. The D50 value, or median value, is defined as the value where half of the population resides above this point, and half resides below this point. For a particle size distribution, the D50 value is the size in microns that splits the distribution with half above and half below this diameter.

Moisture Content Analysis:

The moisture content was measured based on the thermogravimetric (weight loss by heat) method using a moisture analyzer (METTLER TOLEDO, MJ33). The sample (5 g) was added onto the aluminum pan for moisture content measurement. The moisture content was determined when the sample was completely dried on the precision scale under heat.

The product particle structure and morphology was inspected by using a scanning electron microscope (SEM).

Results

Total Oil/Encapsulation Efficiency

Products produced by the HVLCHFAC nozzle at 60° C. (Example 1) and 90° C. (Example 2) both presented in a free-flowing dry powder form and provided better total oil and encapsulation performance than the conventional spray dry control example. Although there was different voltage charging utilized on samples, Example 1 (20 kVAC) and Example 2 (50 kVAC), there was no significant difference in total oil content or encapsulation efficiency due to the charging voltage.

TABLE 2

Total oil/Encapsulation efficiency

| | Total oil (g) | Surface oil (%) | Encapsulation Efficiency (%) |
|---|---|---|---|
| Control 1 | 18.2 | 0.05 | 90.9 |
| Example 1 | 18.6 | 0.02 | 92.8 |
| Example 2 | 18.5 | 0.05 | 92.3 |

TABLE 3

Particle size analysis:

| | D50 (µm) |
|---|---|
| Control 1 | 49.3 |
| Example 1 | 88.6 |
| Example 2 | 85.9 |

Comparing the samples prepared using the present technology (Examples 1 and 2) to the control sample, it was found that the samples provided larger particle sizes overall.

Example 1 and Example 2 have a greater D50, 88.6 µm and 85.9 µm respectively, than the control sample (49.3 µm). There was no significant difference in terms of particle size between Example 1 and Example 2.

TABLE 4

Moisture content

| | Moisture content (%) |
|---|---|
| Control 1 | 1.6 |
| Example 1 | 3.2 |
| Example 2 | 3.0 |

The Example 1 and Example 2 samples had moisture contents of about 3%, as shown in Table 4. Even though they are slightly higher than the control spray dry sample, they are both under an acceptable moisture content limit of 5%.

Figure 7:
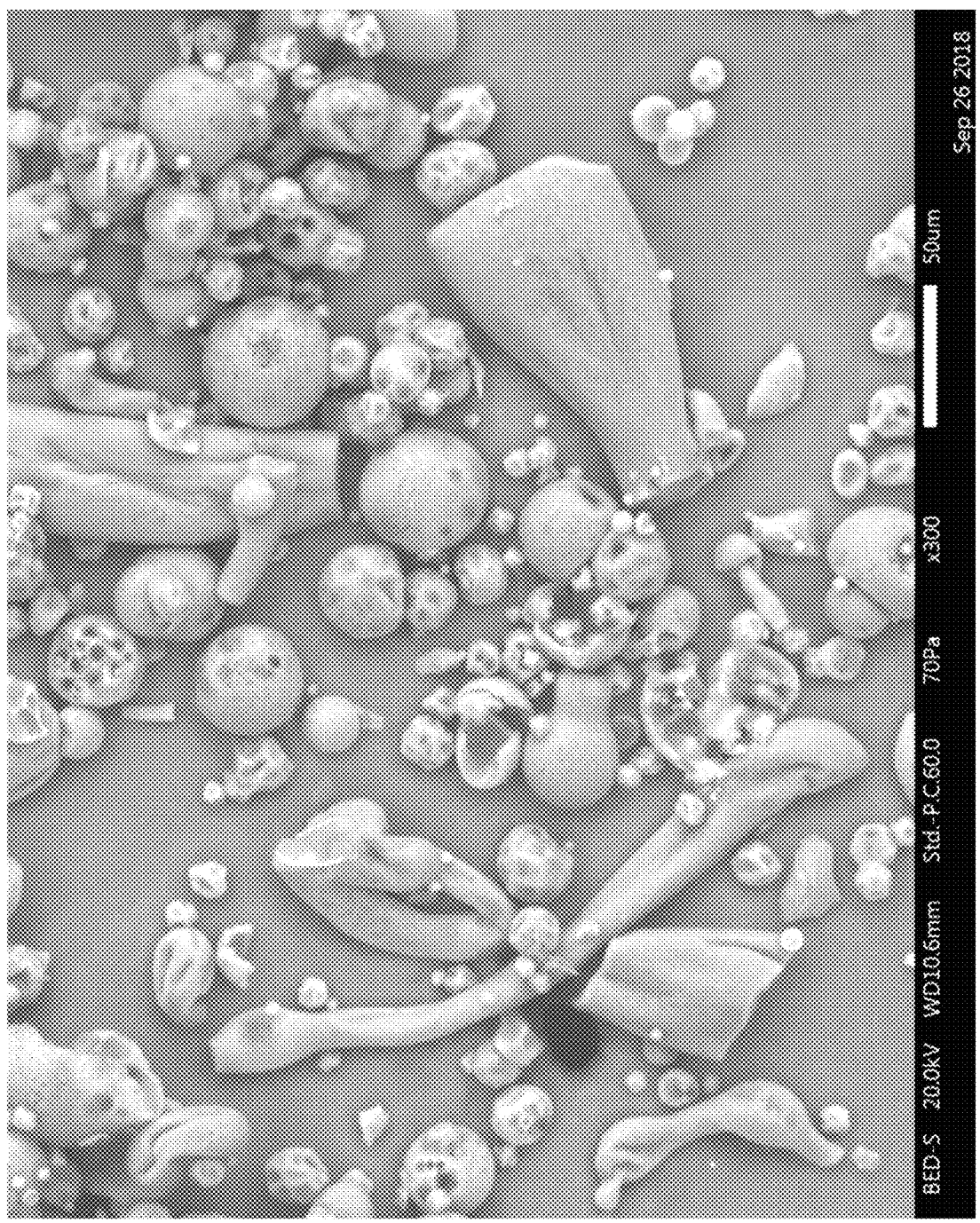
Figure 8:
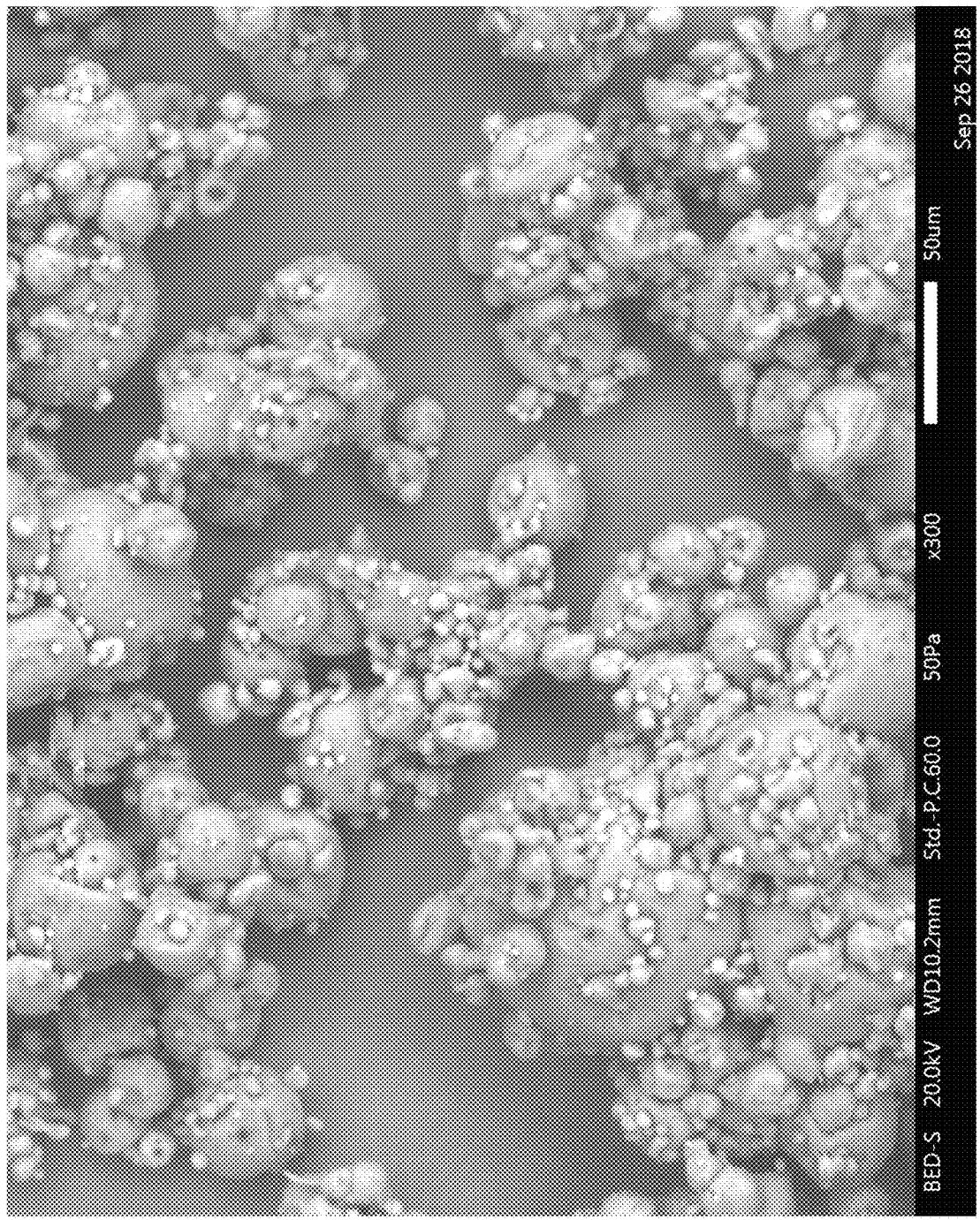
Figure 9:
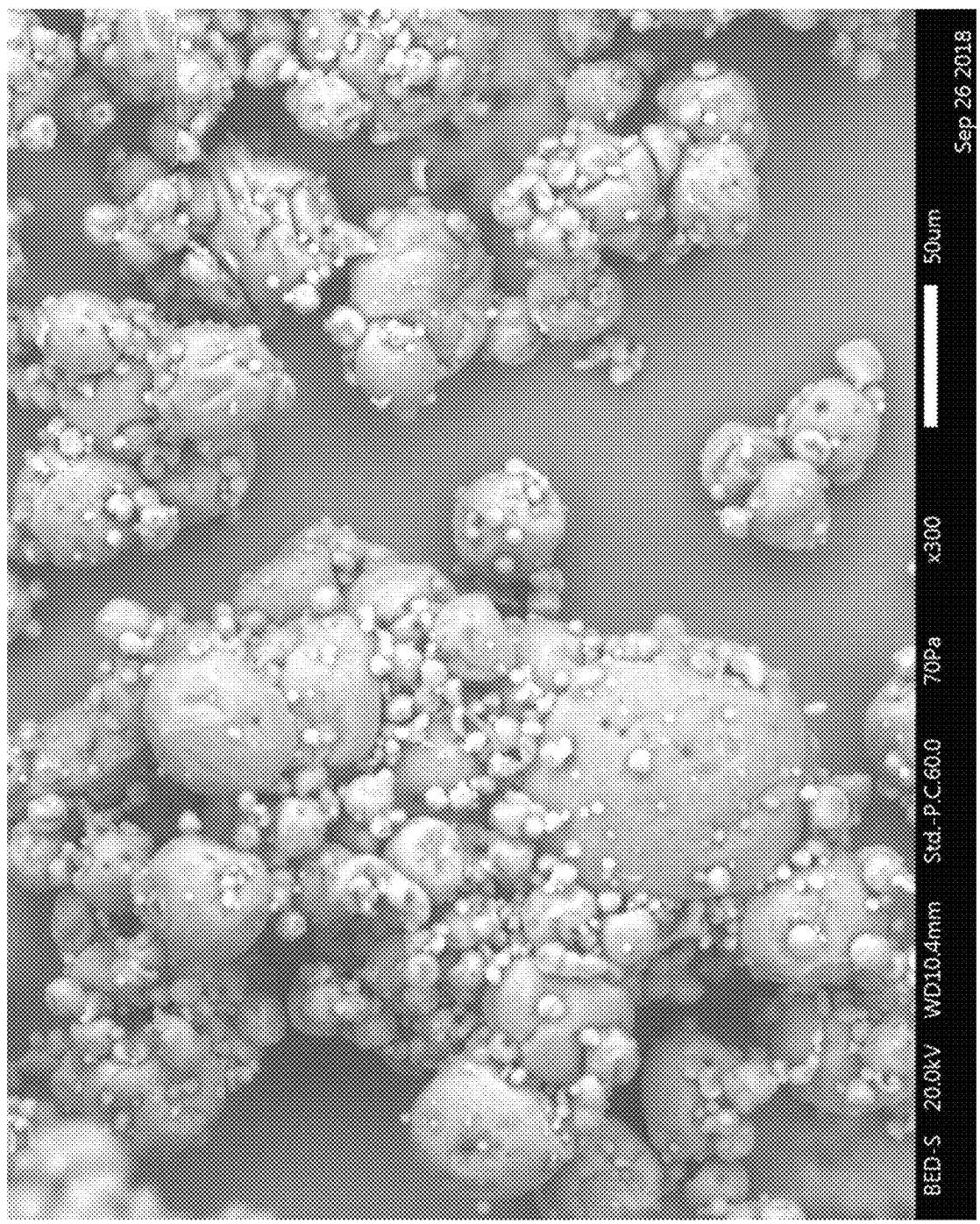

The SEM images that represent the particle structure of samples made with a traditional spray drying process (Control 1) and the present technology (Examples 1 and 2) are shown in FIG. 7, FIG. 8, and FIG. 9, respectively. FIGS. 8 and 9 show that the Example 1 and 2 products resulted in larger agglomerated particles with multiple particles sticking to each other. In contrast, the Control 1 traditional spray dry sample resulted in a discrete sphere structure with smaller particles, as shown in FIG. 7.

Example 3-4

Materials and Methods

Example 3 and Example 4 were created by using the same materials and process as described in Example 1 (20 kVAC charged), and Example 2 (50 kVAC charged) respectively. The water amount used in these Examples was about 150 parts to make an emulsion having a solid content of about 40% solid. The processing parameters are summarized in Table 5.

TABLE 5

Processing Parameters and Observations

| | Example #3 | Example #4 |
|---|---|---|
| Processing parameters: | | |
| | Spraying nozzle | |
| | HVLCHFAC spray nozzle 20 kVAC charged | HVLCHFAC spray nozzle 50 kVAC charged |
| Emulsion solid content (%) | 40 | 40 |
| Inlet temperature (° C.) | 90 | 90 |
| Outlet temperature (° C.) | 50 | 50 |
| Delivering gas | Nitrogen | Nitrogen |
| Atomizing gas pressure (psi) | 60 | 60 |
| Atomizing gas temperature (° C.) | 90 | 90 |

TABLE 5-continued

Processing Parameters and Observations

|  | Example #3 | Example #4 |
|---|---|---|
| Emulsion feeding rate (ml/min) | 180 | 180 |
| Visual appearance of final product | Free flowing powder | Free flowing powder |

Result and Observation

The samples prepared by the present technology with voltage charged at 20 kVAC (Example 3) and 50 kVAC (Example 4) and lower solid contents (40% solid) were both free-flowing dry powders.

In terms of total oil loading and encapsulation efficiency, as shown in the following Table 6, both samples have an encapsulation efficiency greater than the Control sample 1, Example 1 and Example 2, which used a higher solid content emulsion. There was no significant difference in encapsulation efficiency as a result of the different charging voltages, 20 kVAC (Example 3) versus 50 kVAC (Example 4).

TABLE 6

Total oil/Encapsulation efficiency:

|  | Total oil (g) | Surface oil (%) | Encapsulation Efficiency (%) |
|---|---|---|---|
| Example 3 | 19.2 | 0.03 | 95.9 |
| Example 4 | 19.3 | 0.01 | 96.6 |

TABLE 7

Particle size analysis:

|  | D50 (μm) |
|---|---|
| Example 3 | 21.9 |
| Example 4 | 37.7 |

The Example 3 and Example 4 samples had smaller particle sizes and lower D50 compared to the Example 1 and Example 2 samples. It is believed that the lower solid content of the emulsion used in Examples 3 and 4 resulted in smaller atomized emulsion droplets at 60 psi due to a lower viscosity compared to Examples 1 and 2, which used a higher solid content emulsion having a higher emulsion viscosity. To optimize the particle size distribution, the solid content may be adjusted.

TABLE 8

Moisture content

|  | Moisture content (%) |
|---|---|
| Example 3 | 1.7 |
| Example 4 | 2.1 |

The moisture content of Example 3 and Example 4 both showed lower than 5% acceptable moisture content limit, as shown in Table 8.

Figure 10:
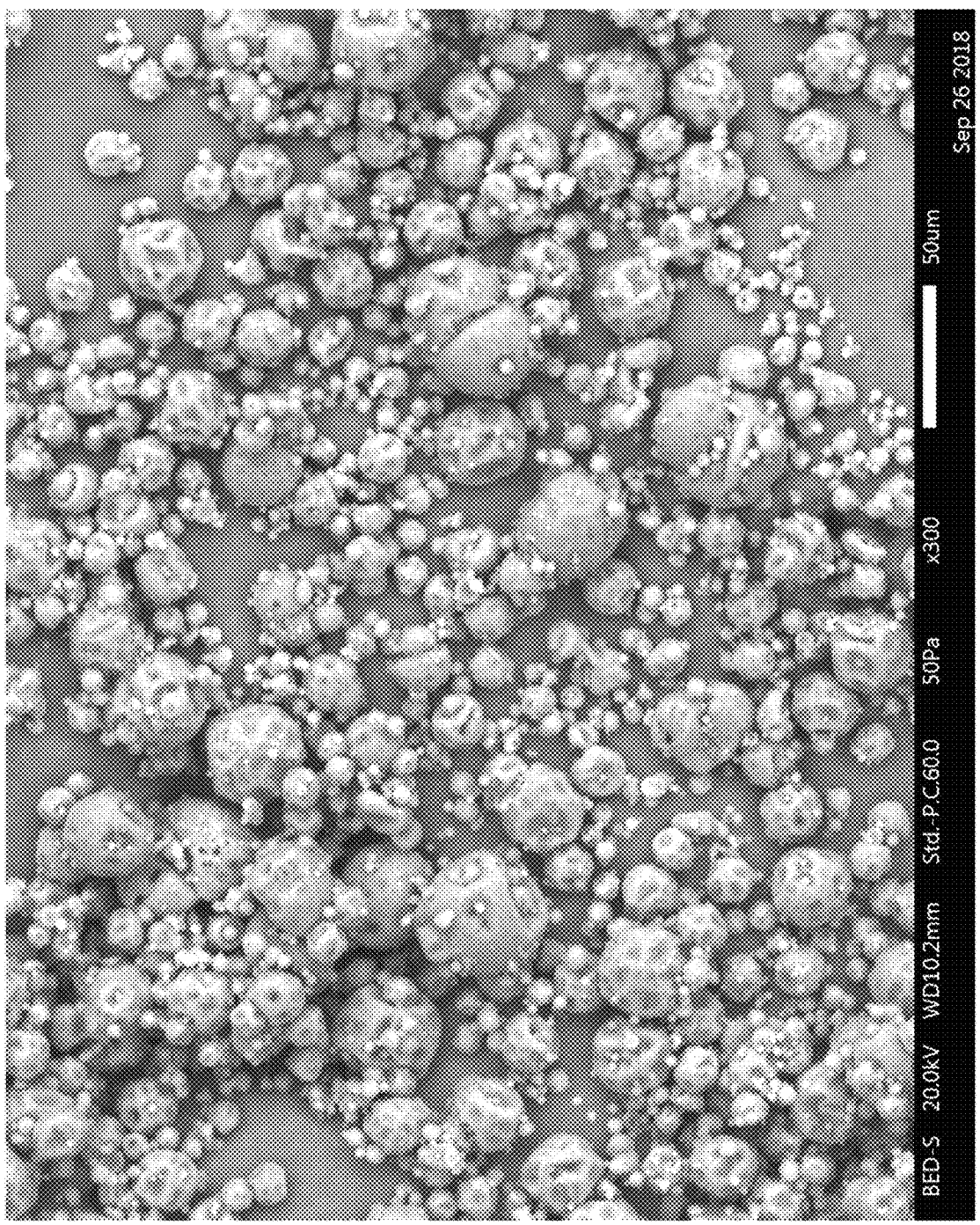
Figure 11:
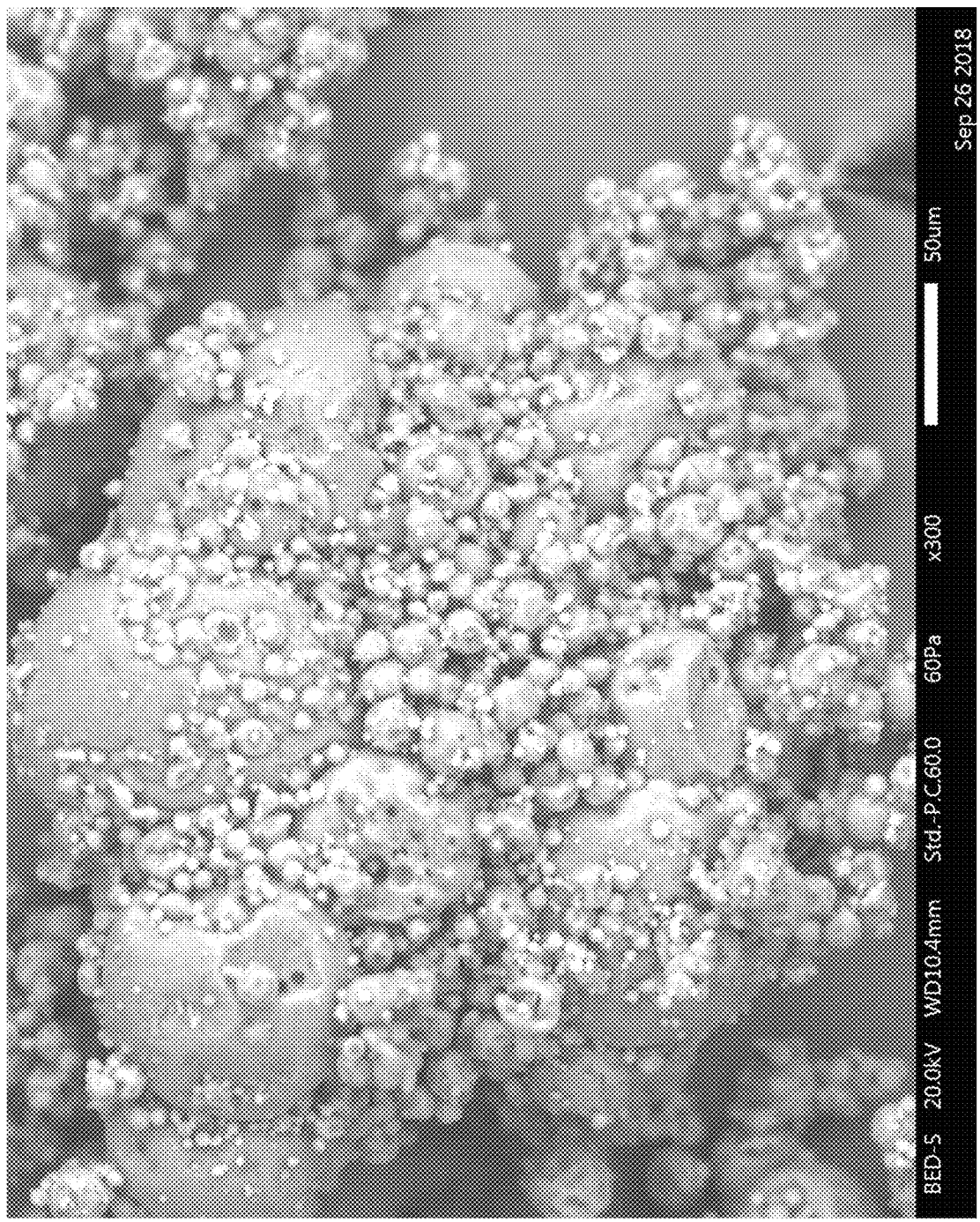
Figure 12:
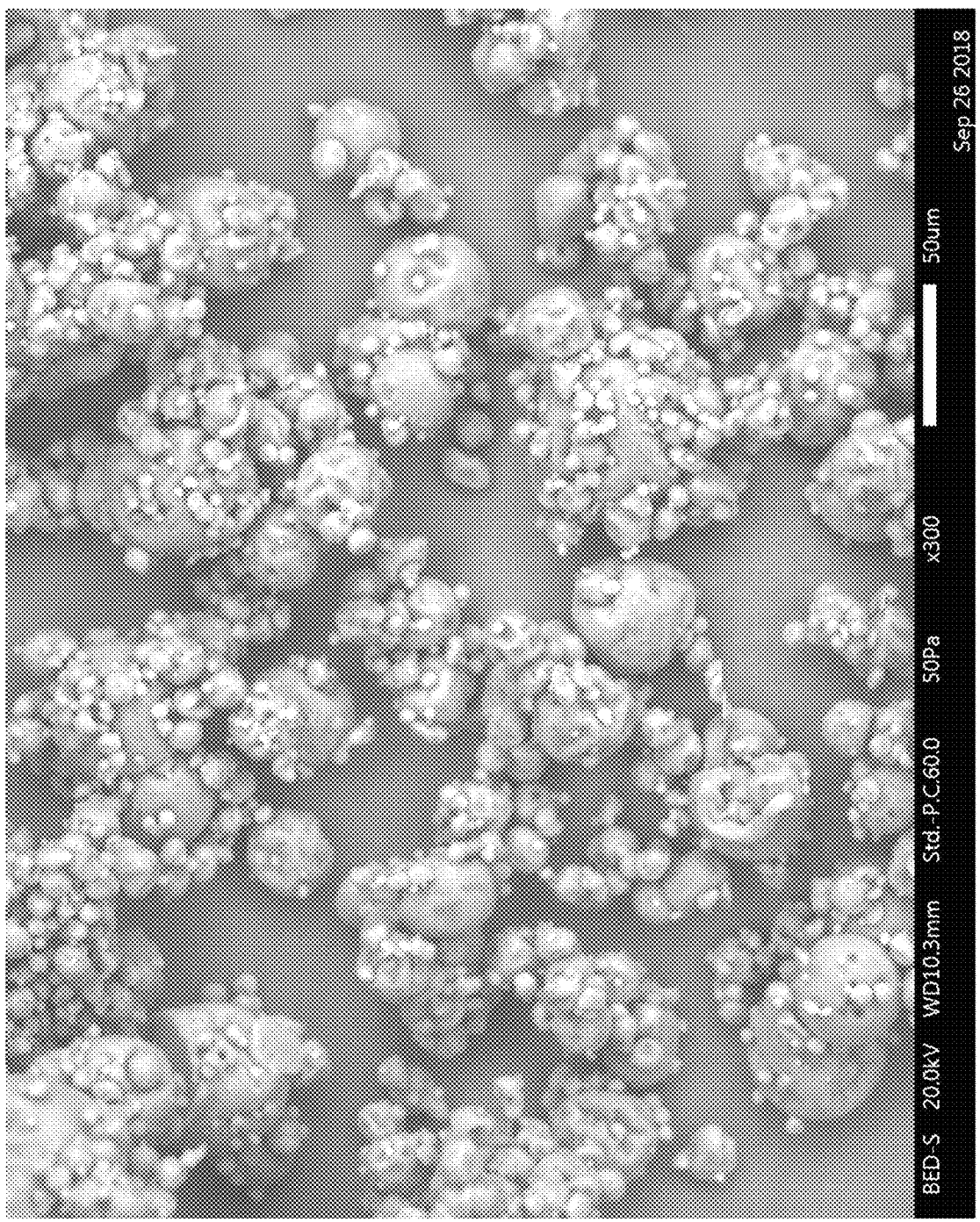
Figure 13:
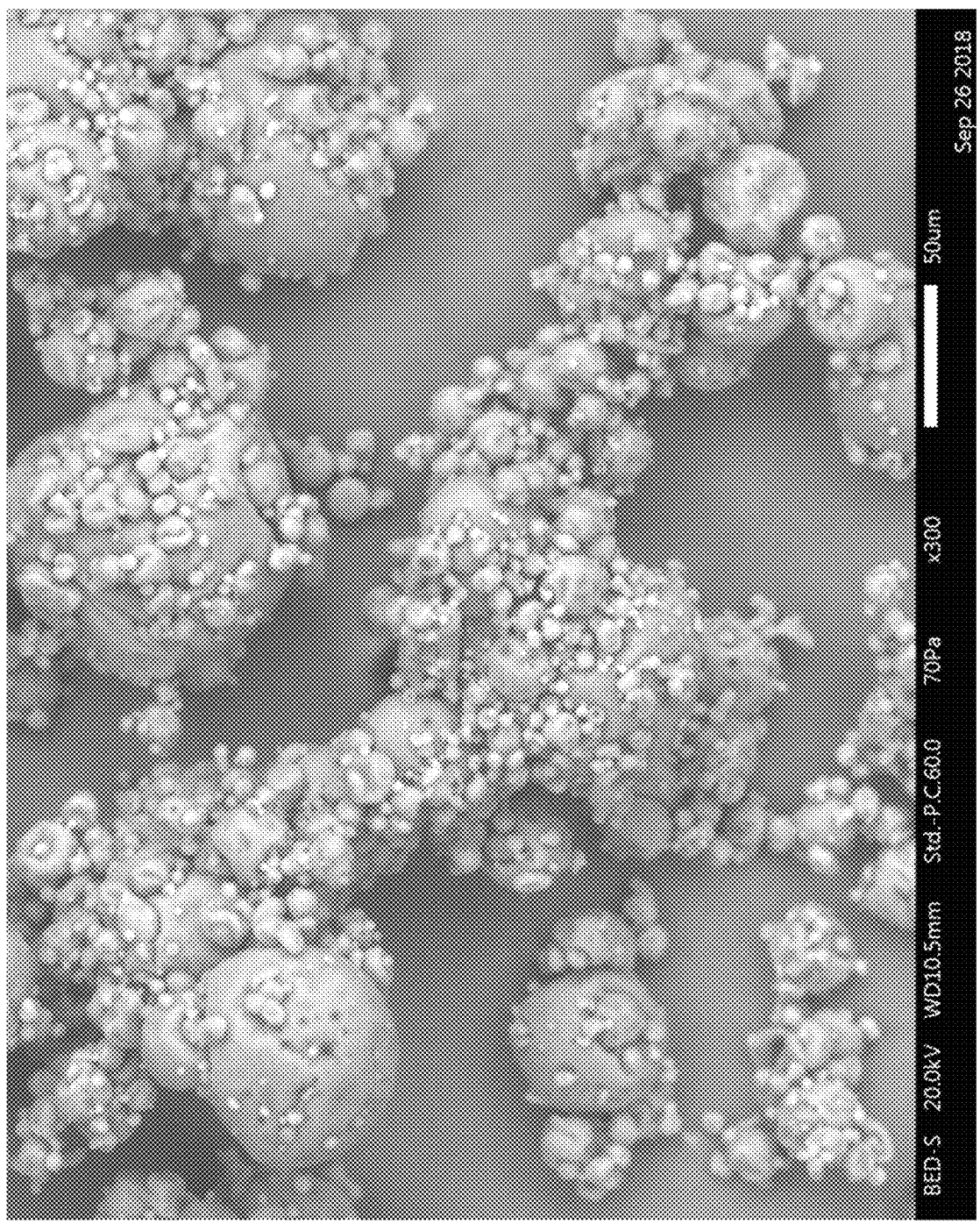
Figure 14:
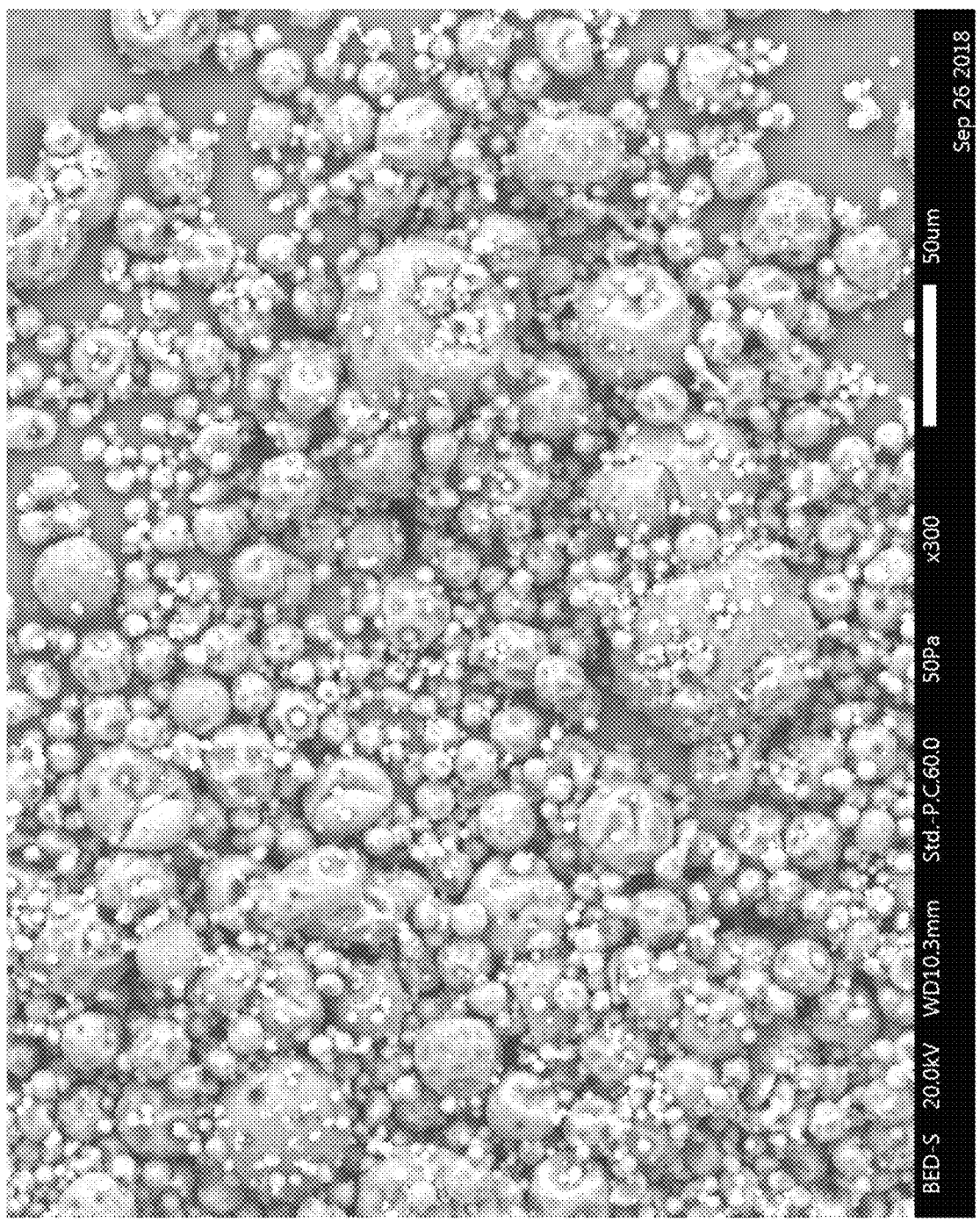

SEM images of the Example 3 and Example 4 samples are shown in FIG. 10 and FIG. 11, respectively. Comparing the particle structure shown in FIG. 10 with that in FIG. 11, it can be seen that, at lower solids content, the difference in charging voltage has an effect on the resulting structure of the spray dried product. The higher voltage charge used in Example 4 helped to promote a more agglomerated particle structure, whereas the lower voltage charge used in Example 3 provided more discrete particles.

Examples 5, 6, 7 and 8: Lower Temperature

Materials and Methods

A series of samples made with same formulation as Examples 1, 2, 3 and 4 were processed at a lower inlet temperature of 60° C. Examples 5 and 6 contained the same amount of emulsion solid content as Example 1 and Example 2 at 55% solids. Example 7 and 8 contained the same amount of emulsion solid content as Examples 3 and 4 at 40% solids. The process parameters are shown in Table 9 below.

TABLE 9

Processing Parameters and Observations

|  | Example #5 | Example #6 | Example #7 | Example #8 |
|---|---|---|---|---|
| Processing parameters: | | | | |
| Spraying nozzle | HVLCHFAC spray nozzle 20 kVAC charged | HVLCHFAC spray nozzle 50 kVAC charged | HVLCHFAC spray nozzle 20 kVAC charged | HVLCHFAC spray nozzle 50 kVAC charged |
| Emulsion solid content (%) | 55 | 55 | 40 | 40 |
| Inlet temperature (° C.) | 60 | 60 | 60 | 60 |
| Outlet temperature (° C.) | 50 | 50 | 50 | 50 |
| Delivering gas | Nitrogen | Nitrogen | Nitrogen | Nitrogen |
| Atomizing gas pressure (psi) | 60 | 60 | 60 | 60 |
| Atomizing gas temperature (° C.) | 90 | 90 | 90 | 90 |
| Emulsion feeding rate (ml/min) | 180 | 180 | 180 | 180 |
| Visual appearance of final product | Free flowing powder | Free flowing powder | Free flowing powder | Free flowing powder |

Result and Observation

All the finished samples were dry after the lower temperature (60° C.) process and collected as free-flowing powder.

Total Oil/Encapsulation Efficiency

Overall, all the samples made with the lower inlet temperature of 60° C. showed encapsulation efficiency higher than the Control 1 sample at 91%. In contrast to using an inlet temperature of 90° C., the charging voltage showed an effect on total oil content and encapsulation efficiency when drying at an inlet temperature 60° C. It was found that, comparing Example 5 to Example 6, the total oil content and encapsulation efficiency decreased with increased charging voltage when the emulsion solids content was at 55%. However, the total oil content and encapsulation efficiency increased with the increased charging voltage as shown in Example 7 and Example 8 when using a lower solids content (40%) emulsion.

TABLE 10

Total Oil/Encapsulation efficiency

|  | Total oil (g) | Encapsulation Efficiency (%) |
| --- | --- | --- |
| Example 5 | 19.0 | 95.0 |
| Example 6 | 18.5 | 92.5 |
| Example 7 | 18.4 | 91.9 |
| Example 8 | 18.8 | 93.9 |

Particle Size:

Overall, the samples made with the lower solid content emulsion (Examples 7 and 8) showed smaller particle sizes than samples made with the higher solid content emulsion (Examples 5 and 6), as shown in Table 11.

TABLE 11

Particle Size

|  | D50 (µm) |
| --- | --- |
| Example 5 | 75.2 |
| Example 6 | 77.3 |
| Example 7 | 20.7 |
| Example 8 | 29.5 |

Moisture Content

TABLE 12

Moisture Content

|  | Moisture content (%) |
| --- | --- |
| Example 5 | 4.1 |
| Example 6 | 4.0 |
| Example 7 | 3.7 |
| Example 8 | 3.0 |

All the samples showed a moisture content lower than the 5% acceptable moisture content limit, which demonstrates the ability to dry the emulsion from liquid to free flowing dry powder at 60° C. using the HVLCHFAC spray nozzle.

Figure 15:
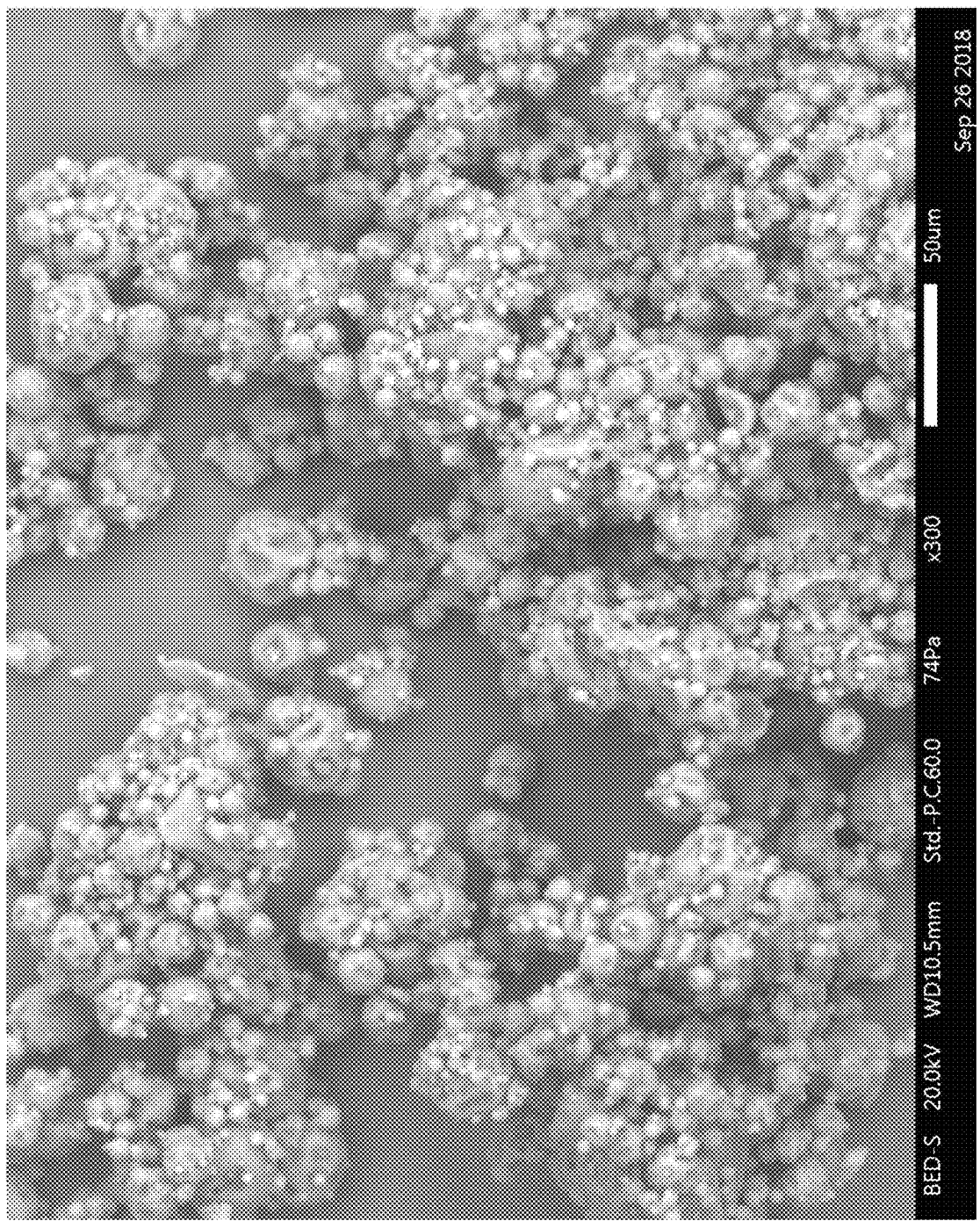

The SEM images of the Example 5, 6, 7, and 8 samples, made using an inlet temperature of 60° C., and with different charge voltages and solids contents, are shown in FIG. 12, FIG. 13, FIG. 14 and FIG. 15, respectively. Comparing FIG. 12 with FIG. 13, it can be seen that, at a solids loading of 55% for the samples, there was no significant difference in particle structure as a result of the different charging voltages (20 kVAC for the FIG. 12 sample and 50 kVAC for the FIG. 13 sample). Both product samples showed an agglomerated structure. However, comparing FIG. 14 with FIG. 15, it can be seen that, at a solids loading of 40% for the samples, there is a difference in particle structure as a result of the different charging voltages (20 kVAC for the FIG. 14 sample and 50 kVAC for the FIG. 15 sample). A higher voltage charge helped to promote agglomeration, as shown in FIG. 15.

The presently described technology and the manner and process of making and using it, are now described in such full, clear, concise and exact terms as to enable one of ordinary skill in the art to which the present technology pertains, to make and use the same. It should be understood that the foregoing describes some embodiments and advantages of the invention and that modifications may be made therein without departing from the spirit and scope of the presently described technology as set forth in the following claims.

The invention claimed is:

1. A spray drying system for drying a liquid into a dried powder, the system comprising:
   (a) a drying chamber having an inlet through which the drying chamber receives a drying gas for drying the liquid, and an outlet through which the dried powder can be collected;
   (b) an atomizer adapted to receive the liquid, and arranged to atomize the liquid into the drying chamber in the form of droplets, which contact the drying gas in the drying chamber;
   (c) a high-voltage alternating-current source in electrical contact with the atomizer and configured to directly impart an electrical charge to the liquid atomized by the atomizer,
   wherein the electrical charge imparted to the liquid atomized by the atomizer is a high-voltage charge.

2. The system of claim 1, wherein the high-voltage alternating-current source is a high-voltage low-current high frequency alternating-current source, where the high-frequency is in the range of 3 MHz to 30 MHz.

3. The system of claim 1, wherein the high-voltage alternating-current source is a high-voltage low-current low frequency alternating-current source, where the low-frequency is in the range of about 50 kHz to 3 MHz.

4. The system of claim 1, wherein a voltage of the high-voltage alternating-current source is in the range of about 2 kVAC to about 200 kVAC.

5. The system of claim 4, wherein a current of the high-voltage low-current alternating-current power source is less than 1 mA.

6. The system of claim 4, wherein the high-voltage alternating-current source is an electrical resonant transformer circuit.

7. The system of claim 1, wherein the atomizer is a dual-fluid spray nozzle, a rotary atomizer nozzle, or a pressurized nozzle.

8. The system of claim 7, wherein the atomizer further includes a liquid inlet for receiving the liquid to be atomized, and a hollow electrode that is in electrical contact with the high voltage alternating current source, and wherein the liquid inlet is coupled to the hollow electrode so that the liquid is received by and travels through the hollow electrode.

9. The system of claim 1, wherein the system further includes a recirculation unit in communication with the inlet and the outlet of the drying chamber, the recirculation unit comprising a condenser, for processing the drying gas exiting from the outlet to remove moisture from the drying gas, and a heater, for heating the processed drying gas prior to introducing the processed drying gas to the inlet of the drying chamber.

10. The system of claim 1, wherein the atomized droplets in the drying chamber form a spray cloud.

11. The system of claim 10, wherein the spray cloud of droplets develops a capacitance.

12. The system of claim 11, wherein the high-voltage alternating-current source is tuned for resonance with the capacitance developed in the spray cloud.

\* \* \* \* \*